(12) United States Patent
Ianiro et al.

(10) Patent No.: US 10,967,034 B2
(45) Date of Patent: Apr. 6, 2021

(54) MUSCADINE TOPICAL COMPOSITION WITH LOW CONTENT OF CONDENSED TANNIN

(71) Applicant: Shaklee Corporation, Pleasanton, CA (US)

(72) Inventors: Teodoro Ianiro, Concord, CA (US); Sonhee C. Park, Pleasanton, CA (US); Ron Flores, San Jose, CA (US); Christos Kyrou, Goshen, NY (US); Laurel A. Fisher, Los Angeles, CA (US)

(73) Assignee: Shaklee Corporation, Pleasanton, CA (US)

( * ) Notice: Subject to any disclaimer, the term of this patent is extended or adjusted under 35 U.S.C. 154(b) by 78 days.

(21) Appl. No.: 16/319,214

(22) PCT Filed: Jul. 18, 2017

(86) PCT No.: PCT/US2017/042661
§ 371 (c)(1),
(2) Date: Jan. 18, 2019

(87) PCT Pub. No.: WO2018/017608
PCT Pub. Date: Jan. 25, 2018

(65) Prior Publication Data
US 2019/0282648 A1 Sep. 19, 2019

Related U.S. Application Data

(60) Provisional application No. 62/505,543, filed on May 12, 2017, provisional application No. 62/364,222, filed on Jul. 19, 2016.

(51) Int. Cl.
| | | |
|---|---|---|
| *A61K 36/87* | (2006.01) | |
| *A61P 29/00* | (2006.01) | |
| *A61K 9/00* | (2006.01) | |
| *A61K 8/73* | (2006.01) | |
| *A61K 8/67* | (2006.01) | |
| *A61K 8/49* | (2006.01) | |
| *A61K 8/368* | (2006.01) | |
| *A61Q 17/04* | (2006.01) | |
| *A61K 8/42* | (2006.01) | |
| *A61Q 19/00* | (2006.01) | |

(52) U.S. Cl.
CPC .............. *A61K 36/87* (2013.01); *A61K 8/368* (2013.01); *A61K 8/42* (2013.01); *A61K 8/498* (2013.01); *A61K 8/671* (2013.01); *A61K 8/676* (2013.01); *A61K 8/678* (2013.01); *A61K 8/73* (2013.01); *A61K 9/0014* (2013.01); *A61P 29/00* (2018.01); *A61Q 17/04* (2013.01); *A61Q 19/00* (2013.01); *A61K 2800/522* (2013.01)

(58) Field of Classification Search
None
See application file for complete search history.

(56) References Cited

U.S. PATENT DOCUMENTS

| | | |
|---|---|---|
| 6,190,716 B1 | 2/2001 | Galbreath, Jr. |
| 6,638,545 B1 | 10/2003 | Rombi |
| 8,017,147 B2 | 9/2011 | Mazed et al. |
| 8,075,929 B2 | 12/2011 | Shrikhande et al. |
| 8,114,445 B2 | 2/2012 | Hastings |
| 8,173,181 B2 | 5/2012 | Ferguson et al. |
| 8,182,849 B2 | 5/2012 | Endo et al. |
| 8,512,771 B2 | 8/2013 | Ianiro et al. |
| 8,568,804 B2 | 10/2013 | Fisher et al. |
| 8,911,804 B2 | 12/2014 | Fisher et al. |
| 9,132,162 B2 | 9/2015 | Fisher et al. |
| 9,173,916 B2 | 11/2015 | Ianiro et al. |

(Continued)

FOREIGN PATENT DOCUMENTS

| | | |
|---|---|---|
| CN | 1343100 A | 4/2002 |
| CN | 1698733 A | 11/2005 |

(Continued)

OTHER PUBLICATIONS

Bralley et al., "Topical anti-inflammatory activities of *Vitis rotundifolia* (muscadine grape) extracts in the tetradecanoylphorbol acetate model of ear inflammation," *Journal of Medicinal Food* (4): 636-642 (2007).
Greenspan et al., "Anti-inflammatory properties of the muscadine grape (*Vitis rotundifolia*)," *Journal of Agricultural and Food Chemistry* 53(22): 8481-8484 (2005).
Ogino et al., "Wine Manufacturing Process of Using Membrane Filters," *J. Brew. Soc. Japan* 82(11): 819-824 (1987) (English abstract).
Cardona et al., "Color and Polyphenolic Stability in Extracts Produced from Muscadine Grape (*Vitis rotundifolia*) Pomace," *J. Agriculture and Food Chemistry*, vol. 57:8421-8425 (2009).

(Continued)

*Primary Examiner* — Russell G Fiebig
(74) *Attorney, Agent, or Firm* — Klarquist Sparkman, LLP

(57) ABSTRACT

A method for decolorizing a muscadine pomace grape extract by processing the clarified extract by ultrafiltration through a 500-5000 kDa microfiltration membrane to obtain a first permeate in which flavor components are removed. The retentate is subjected to ultrafiltration through a 25-100 kDa ultrafiltration membrane to obtain a second permeate and a second retentate. The polymeric condensed tannins are removed in the second retentate and the second permeate is the decolorized extract having increased levels of polyphenols and lowered levels of sugars and condensed tannins compared to the first retentate. The decolorized extract can be incorporated into skin care compositions, which can also include beta-glucan and grape seed extract. The skin care compositions can and applied to the skin to maintain healthy skin without discoloration, protecting against ultraviolet radiation, and inhibiting the production of anti-inflammatory mediators in skin cells.

30 Claims, 19 Drawing Sheets

(56) References Cited

U.S. PATENT DOCUMENTS

| | | |
|---|---|---|
| 9,421,189 B2 | 8/2016 | Ianiro et al. |
| 2004/0137094 A1 | 7/2004 | Mower et al. |
| 2004/0234671 A1 | 11/2004 | Ector et al. |
| 2005/0158376 A1 | 7/2005 | Sardi et al. |
| 2006/0024392 A1 | 2/2006 | Magnuson et al. |
| 2006/0121137 A1 | 6/2006 | Hartle et al. |
| 2006/0277887 A1 | 12/2006 | Dalton et al. |
| 2007/0003644 A1 | 1/2007 | Randhava et al. |
| 2009/0176718 A1 | 7/2009 | Ribnicky et al. |
| 2010/0004344 A1 | 1/2010 | Dallas |
| 2010/0297741 A1 | 11/2010 | Shrikhande et al. |
| 2011/0177182 A1 | 7/2011 | Ianiro et al. |
| 2011/0177183 A1 | 7/2011 | Ianiro et al. |
| 2012/0045406 A1 | 2/2012 | Urban et al. |
| 2013/0202725 A1 | 8/2013 | Ianiro et al. |
| 2018/0325804 A1* | 11/2018 | Park ...................... A61K 8/676 |

FOREIGN PATENT DOCUMENTS

| | | |
|---|---|---|
| CN | 1956733 A | 5/2007 |
| JP | 2002293736 A | 10/2002 |
| JP | A 2009-535436 | 10/2009 |
| JP | A 2012-51944 | 3/2012 |
| JP | A 2013-504607 | 2/2013 |
| WO | WO 1998/17250 A1 | 5/1997 |
| WO | WO 2005/099761 A1 | 10/2005 |
| WO | WO 2005/110404 A2 | 11/2005 |
| WO | WO 2007/074472 A2 | 7/2007 |
| WO | WO 2007/128558 A1 | 11/2007 |
| WO | WO 2008/144019 | 11/2008 |
| WO | WO 2011/032502 A1 | 3/2011 |
| WO | WO 2015/184291 A1 | 12/2015 |
| WO | WO-2015184291 A1 * | 12/2015 ................ A61P 9/00 |

OTHER PUBLICATIONS

Carroll, "Evaluation of Sparkling Wines Produced from Muscadine Cultivars (*Vitis rotundifolia* Michx)", *Am. J. Enol. Vitic.*, vol. 35/2, pp. 72-74 (1984).

Chen et al., "High-speed Counter-Current Chromatography Separation and Purification of Resveratrol and Piceid from Polygonum Cuspidatum," *J. of Chromatography A*, vol. 907:343-346 (2001).

Dansby, "Evaluation of the Antioxidant and Biological Properties of Muscadine Grape Seed Extracts," *Dissertation North Carolina State University*, pp. ii-v, 1, 45 (2006).

Ector et al., "Resveratrol Concentration in Muscadine Berries, Juice, Pomace, Purees, Seeds and Wines," *Am. J. Enol. Vitic.*, vol. 47(1):57-62 (1996).

Ghanim et al. "A Resveratrol and Polyphenol Inflammatory Stress Response to a Preparation Suppresses Oxidative and High-Fat, High-Carbohydrate Meal," *J. Clin. Endocrinol Metab.*, vol. 96(5):1409-1414 (2011).

God et al., "Anticancer Effects of Four Varieties of Muscadine Grapes," *J. of Medical Food* 10(1):54-59 (2007).

Hudson et al., "Inhibition of Prostate Cancer Growth by Muscadine Grape Skin Extract and Resveratrol through Distinct Mechanisms," *Cancer Research* 67(17):8396-8405 (2007).

Ke-lin, "Impact of Grape Seed Extract on Human Health," *China Drinks*, pp. 46-47 (2003).

Kurilich et al., "Plasma and Urine Responses Are Lower for Acylated vs. Nonacylated Anthocyanins from Raw and Cooked Purple Carrots," *J. Agric. Food Chem.* 53(16):6537-6542 (2005).

Lamikanra, "Development of Anthocyanin Pigments in Muscadine Grapes," *HortScience*, vol. 23/3, pp. 597-599 (1988).

Lopez-Alacron et al., "Evaluating the antioxidant capacity of natural products: A review on chemical and cellular-based assays," *Anlytica Acta*, vol. 763, pp. 661-666 (2013).

Mertens-Talcott et al., Low Concentrations of Quercetin and Ellagic Acid Synergistically Influence Proliferation, Cytotoxicity and Apoptosis in MOLT-4 Human Leukemia Cells, *J. Nutrition* 133:2669-2674 (2003).

Mertens-Talcott et al., "Ellagic Acid and Quercetin Interact Synergistically with Resveratrol in the Induction of Apoptosis and Cause Transient Cell Cycle Arrest in Human Leukemia Cells," *Cancer Letters* 218:141-151 (2005).

Olshansky et al. "Position Statement on Human Aging," http://www.quackwatch.com/01QuackeryRelatedTopics/antiagingpp.html—accessed May 2014.

Pastrana-Bonilla et al., "Phenolic Content and Antioxidant Capacity of Muscadine Grapes," *J. Agricultural and Food Chemistry*, vol. 51:5497-5503 (2003).

Percival and Sims, "Wine Modifies the Effects of Alcohol on Immune Cells of Mice," *J. Nutrition*, vol. 130(5):1091-1094 (2000).

Perron and Brumaghim, "A Review of the Antioxidant Mechanisms of Polyphenol Compounds Related to Iron Binding," *Cell Biochem Biophys*, 53:75-100 (2009).

Ponce, "Chemical and Economic Analysis of Value-Added Product from Muscadine Grape Pomace," *University of Florida* http://ufdc.ufl.edu/UFE0021495/00001 (2007) *Not catalogued until Apr. 2, 2010.

Sandhu and Gu, Antioxidant Capacity, Phenolic Content, and Profiling of Phenolic Compounds in the Seeds, Skin, and Pulp of *Vitis rotundifolia* (Muscadine Grapes) As Determined by HPLC-DAD-ESI-MS", *J. of Agriculture and Food Chemistry*, vol. 58:4681-4692 (2010).

Sapcanin et al., "Antioxidant Capacity in the Lipophilic Fraction of Alzheimer's Brain Tissues," *Bosnian J. Basic Medical Sciences* 7(4):317-321 (2007).

Sikora, "Rejuvenation of Senescent Cells—The Road to Postponing Human Aging and Age-Related Disease?," *Experimental Gerontology*, vol. 48, pp. 661-666 (2013).

Sistrunk et al., "Quality Acceptance of Juices of Two Cultivars of Muscadine Grapes Mixed with Other Juices," *J. Amer. Soc. Hort. Sci,*. vol. 110/3, pp. 328-332 (1985).

Soleas et al., "Comparative Evaluation of Four Methods for Assay of cis- and trans-Resveratrol," *Am. J. Enol. Vitic.*, vol. 48(2):169-176 (1997).

Soto et al., "Recovery and Concentration of Antioxidants from Winery Wastes," *Molecules* 17:3008-3024 (2012).

Talcott et al., "Ellagic Acid and Flavonoid Antioxidant Content of Muscadine Wine and Juice," *J. Agric. Food Chem*, vol. 50, pp. 3186-3192 (2002).

Vashisth, "Evaluation of Drying Technologies for Muscadine Pomace to Produce an Antioxidant Rich Functional Food Ingredient," *The University of Georgia* http://hdl.handle.net/10724/11195 (2009).

Xiao-jia et al., "Review on Health Function, Processing Technology and Determination of Resveratrol," *Food Research and Development*, vol. 27(2):123-126(2006).

Yilmaz and Toledo, "Major Flavonoids in Grape Seeds and Skins: Antioxidant Capacity of Catechin, Epicatechin, and Gallic Acid," *J. Agric. Food. Chem.*, vol. 52:255-260 (2004).

http://thefreedictionary.com/pomace—accessed May 2014.

Gkogkolou and Böhm., "Advanced glycation end products," *Dermato-Endocrinology* 4(3): 259-270 (Jul.-Dec. 2012).

Plundrich et al., "Bioactive polyphenols from muscadine grape and blackcurrant stably concentrated onto protein-rich matrices for topical applications," *International Journal of Cosmetic Science* 35(4): 394-401 (e-PUB Jun. 6, 2013)(Abstract only).

International Search Report from parent PCT Application No. PCT/US2017/042661, 5 pages (dated Nov. 2, 2017).

Written Opinion from parent PCT Application No. PCT/US2017/042661, 7 pages (dated Nov. 2, 2017).

* cited by examiner

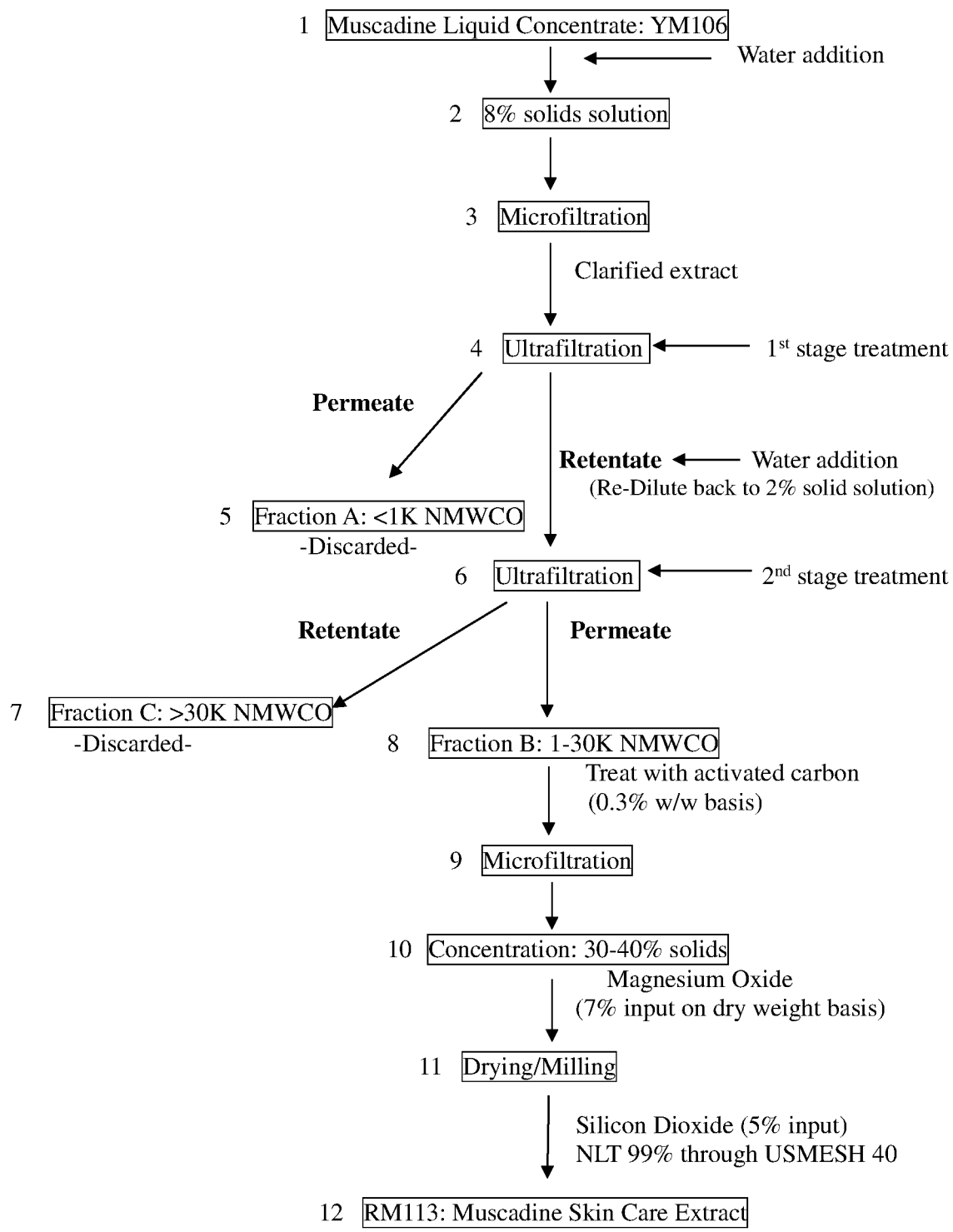

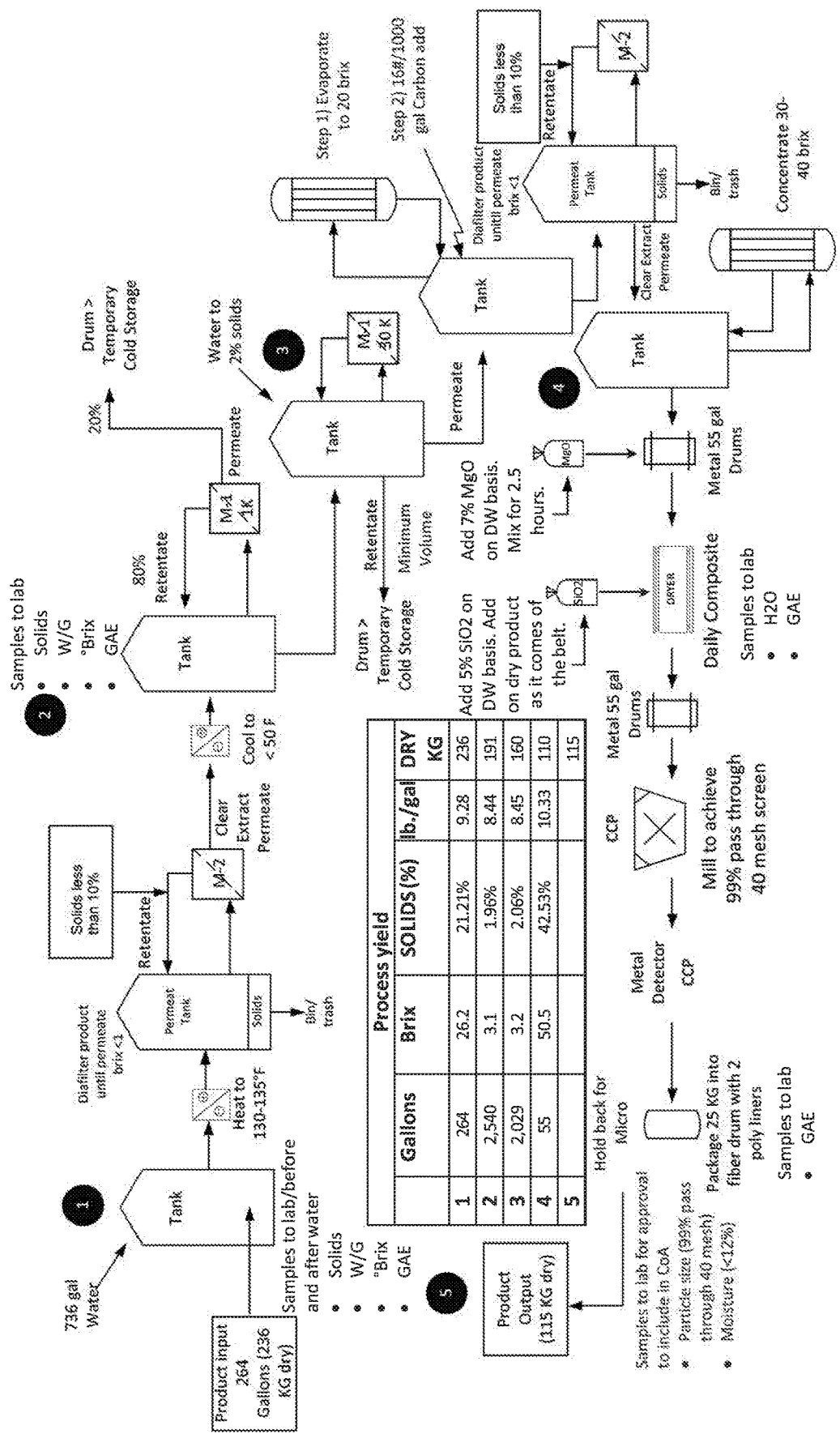
FIG. 2 De-colorized Muscadine Fruit Extract

FIG. 4

Bioassays—Measuring supportive mode of actions on benefits on Skin Health by Muscadine Pomace Extract (Used 1% - 0.000005% Novel, decolorized Muscadine pomace extract)

| | Measurement | Benefit Area | Results | Cells / Methods Used | Comments |
|---|---|---|---|---|---|
| 1 | Elastase | Elasticity | Effective: IC50-0.056% | Non-cell / Spec (405nm) | 100% inhibition by 1 and 0.5% |
| 2 | Collagenase | Firmness | Effective: IC50-0.28% | Non-cell / Spec (421 nm) | |
| 3 | DPPH | Antioxidant | Effective: Trolox Equivalent (TE) about 2,000 | Non-cell / Spec (517 nm) | TE highest in 1 and 0.5% - closed to TE2,000 |
| 4 | TT dimer | Prevention of DNA damage | Effective: * 1% worked for both damage prevention and repair; 0.1% worked for DNA damage prevention, but no effect on the repair. | MatTek EpiDerm (Epi-200) tissue ME treat before UVB insult for DNA damage protection; After UVB insult for DNA repair | ME Pretreatment with 1% ME before UVB insult worked THE BEST – no TT dimer formation like without UVB insult. |
| 5 | Keratinocyte viability | Cell Viability / Renewal?? | Effective: * at 0.1, 0.05, 0.01% | Keratinocyte / MTT after UVB exposure | 0.1, 0.05% are better than 20uM Trolox. 0.1% is like without UVB exposure. |
| 6 | Tyrosinase | Prevent Dark Spot / hyperpigmentation | To be effective IC50 at 1.48% | Non-cell / Spec (490 nm) | Max conc used is 1% showing about 35% inhibition |

MUSCADINE TOPICAL COMPOSITION WITH LOW CONTENT OF CONDENSED TANNIN

CROSS REFERENCE TO RELATED APPLICATIONS

This is a § 371 U.S. national stage of International Application No. PCT/US2017/042661, filed Jul. 18, 2017, which was published in English under PCT Article 21(2), and which application claims priority to U.S. Provisional Application No. 62/364,222, filed Jul. 19, 2016 and U.S. Provisional Application No. 62/505,543, filed May 12, 2017, which are incorporated by reference herein in their entirety.

FIELD

This disclosure relates to grape pomace extracts, such as muscadine (*Vitis rotundifolia*) pomace solvent extracts, grape pomace extraction processes, and methods of obtaining fractions of grape pomace extracts, such as muscadine grape pomace extracts, suitable for use in skin care products. This disclosure also relates to topical compositions that contain decolorized muscadine pomace solvent extract, beta-glucan and grape seed extract, which reduce inflammation when applied to the skin, and to methods of reducing skin inflammation using the topical compositions.

BACKGROUND

Grape extracts are known to have beneficial antioxidant properties. Muscadine grapes, for example, contain several bioactive polyphenolic compounds, including flavonoids (such as flavonols, anthocyanins, and flavanones, as well as flavan-3-ols and oligomers thereof known as proanthocyanidins) and non-flavonoids (such as phenolic acids, tannins and stilbene derivatives, for example resveratrol). The protective and anti-inflammatory effects of the flavonoids are believed to be due to free radical scavenging, beneficial effects on cellular signaling pathways and gene expression, and selective interference with the cell division cycle of rapidly and abnormally proliferating mammalian cells.

The beneficial properties of grape extracts have led to their use in nutraceuticals. U.S. Pat. No. 6,190,716 disclosed a muscadine grape dietary supplement that was obtained by crushing and de juicing muscadine grapes then breaking down the pulp with heat and enzymes. U.S. Pat. No. 6,638,545 disclosed a grape extract having a rich polyphenol content for use as a dietary supplement and cosmetic composition. U.S. Pat. Nos. 8,568,804, 9,132,162 and 9,173,916 disclosed a composition in which a pomace extract of bronze and purple muscadine grapes was shown to have enhanced anti-oxidant activity.

Although it is recognized that muscadine and other red grape extracts have excellent antioxidant activities, their use in topical compositions has been limited by the elevated level of tannins in the extracts. The term "tannin" was originally applied to this class of compounds because of the use of astringent wood tannins to "tan" animal hides into leather. Red grape tannins taste dry and astringent, and the tannins impart color to wine. When included in topical grape extract preparations the tannins discolor the composition as well as the skin to which they are applied.

In terms of their chemical composition, tannins are divided into the hydrolyzable tannins and the condensed tannins or flavonoids. The hydrolyzable tannins are polymerized simple phenolic substances, such as esters of gallic acid and of dimers thereof (digallic acid, ellagic acid). The hydrolyzable tannin can be further divided into gallotannins that yield gallic acid after hydrolysis, and ellagitannins that release ellagic acid after hydrolysis. In contrast to the hydrolyzable tannins, the condensed tannins are not decomposable by hydrolysis. On the contrary, when subjected to heating in an acidic medium they progressively polymerize and form amorphous anthocyanin pigments, of red color, or insoluble yellow-brown products, of high molecular mass, called phlobaphenes.

In addition to their deep color, condensed tannins have more hydroxyl groups and a larger molecular structure than most other polyphenolic organic compounds, which enable them to effectively trap and retain malodorous molecules. This property has discouraged the use of grape extracts in topical preparations, such as antioxidant or cosmetic compositions.

The process of skin inflammation is complex. When the skin is exposed to a "triggering" stimulus, such as ultraviolet (UV) radiation, an irritant, or to allergens, the cells in the skin produce a variety of inflammatory cytokines and chemokines. These cytokines and chemokines bind to specific receptors on target cells and stimulate the production of additional inflammatory mediators, which cause vasodilation and activate nerve cells. The expression of cytokines and chemokines by inflammatory cells also results in the production of enzymes, free radicals, and other biological mediators that damage the skin. The end result of the initial triggering event is the amplification of a large inflammatory response that, while designed to help the skin fight infection from invading bacteria, actually causes considerable damage to the skin. A need remains for topical compositions that have reduced tannins and can be used to decrease skin inflammation.

SUMMARY

Methods and compositions are disclosed herein for producing a decolorized grape solvent extract composition, such as a decolorized muscadine grape solvent extract composition. The present disclosure enables the preparation of grape pomace extracts, including, but not limited to, combinations of different muscadine grape extracts, which have a lower condensed tannin content while substantially preserving polyphenols and desirable antioxidant activity in the extract. The resulting antioxidant extracts are less prone to discoloring skin and have an improved odor as compared to prior grape pomace extracts, such as prior muscadine grape pomace extracts. In some examples, the decolorized extract is obtained from both bronze and/or purple muscadine grape pomace.

In one example, the method lowers a condensed tannin content of a precursor grape extract, such as a precursor grape pomace extract, for example a precursor muscadine grape pomace extract, and decolorizes the extract. The precursor extract, such as the precursor muscadine grape pomace extract, is clarified by microfiltration to remove solids and the clarified extract is processed by ultrafiltration through a 500-5000 kDa microfiltration membrane to obtain a first permeate and a first retentate. Flavor components are removed in the first permeate, and the first retentate is processed by ultrafiltration through a 25-100 kDa ultrafiltration membrane to obtain a second permeate and a second retentate. The polymeric condensed tannins are removed in the second retentate and the second permeate is the decolorized extract having increased levels of polyphenols and lowered levels of sugars and condensed tannins compared to the first retentate.

In some examples, the decolorized extract is treated with an odor-reducing agent, such as activated charcoal, calcium alginate, bentonite, or aluminosilicate absorbents. The decolorized extract can also be exposed to magnesium oxide to mineralize organic acids in the decolorized extract. The decolorized extract may also be dried and milled.

In particular examples, the precursor grape pomace extract is a muscadine grape pomace extract, for example a combination of precursor extracts of bronze and purple muscadine grape pomace. In some embodiments of the precursor extract, the ratio of bronze muscadine pomace extract to purple muscadine pomace extract ranges from 0.1 to 10 (weight to weight), such as from 0.3 to 3 (weight to weight).

The decolorized extract may be any extract obtained by the foregoing decolorization process. Alternatively, the decolorized extract comprises 9-10% polyphenols and less than 4% monosaccharides, wherein the condensed tannins are less than 10% of the total polyphenol content of the decolorized grape extract, such as a grape pomace extract, for example a muscadine grape pomace extract. In some examples, the total polyphenols in the decolorized extract consist of at least 90% polyphenols other than condensed tannins. In other examples, the decolorized muscadine grape pomace extract contains 0.5-2% fiber, 7-9% protein, 0.5-1.5% fat, and 15-17% organic acids, such as 1-2% fiber, 7-8% protein, 0.05-0.5% fat, and 15.5-16.5% organic acids. In some examples, the phenolic content of the extract comprises 2-3% ellagic acid and 30-31% gallic acid, for example: 2-3% ellagic acid, 3-4% ellagic acid glycosides, 30-31% gallic acid, 2-3% quercetin, 10-11% gallotannins, 7-8% ellagitannins, 29-30% proanthocyanidins, 4-5% anthocyanins, 2-3% catechins, and 6-7% phenolic acids.

Also disclosed are skin care compositions that include the decolorized muscadine grape pomace extract, and methods of maintaining healthy skin by applying the skin care composition in a sufficient amount to the skin for a sufficient period of time to improve one or more of elastase inhibition, collagenase inhibition, antioxidant activity, reduced DNA damage, enhanced DNA repair, increased cell survival after exposure to ultraviolet radiation, or increased tyrosinase inhibition. Topical compositions, made with decolorized grape solvent extracts prepared as disclosed herein, have antioxidant activity.

In response to UV radiation or other pro-inflammatory stimuli, keratinocytes can release cytokines to help direct immune cells to the site of the injury. Inflammatory pathways in the skin also involve prostaglandins, including prostaglandin E2, which are synthesized from arachidonic acid via the action of cyclooxygenases. Inflammation in dermal and epidermal cells, including keratinocytes, can be monitored by the presence or absence of these cytokines and prostaglandins. Cytokines released by keratinocytes include TNF alpha, and the interleukins IL-1 alpha, IL-1 beta, IL-3, IL-6, IL-7, IL-8, IL-10, IL-18, and IL-1RA. Prostaglandin E2 (PGE2) has been shown to be involved in the inflammatory pathway of the skin and can also be used as a marker, along with the cytokines referenced above, to indicate the efficacy of topical anti-inflammatory compositions.

Topical compositions that reduce the levels of markers of inflammation, and methods of reducing inflammation using a topical composition, are disclosed herein. In some embodiments, the compositions disclosed herein reduce skin inflammation after they are applied topically to the skin. The reduction of inflammation can be due to the reduction in the production of IL-1 alpha, IL-6, prostaglandin E2, or any combination thereof, in a treated skin cell as compared to a control cell. In some non-limiting examples, the control cell can be a cell treated with an inactive carrier compound, or it may be an untreated cell. In some examples, the inflammation is a result of UV radiation, including ultraviolet A (UVA) and ultraviolet B (UVB) radiation.

Advances in the production of decolorized grape solvent extracts allow for the use of such grape extracts in topical preparations, including for skin care products. The present disclosure provides topical compositions that include a decolorized grape pomace extract that has a lower condensed tannin content while substantially preserving polyphenols and desirable anti-inflammatory activity in the extract. In some examples, the decolorized extract is obtained from both bronze and/or purple muscadine (*Vitis rotundifolia*) grape pomace. The presently disclosed compositions also can include grape seed extract and beta-glucan.

In some embodiments, the topical compositions include an effective amount of decolorized muscadine (*Vitis rotundifolia*) pomace solvent extract, beta-glucan and grape seed extract, wherein the decolorized muscadine pomace solvent extract comprises a liquid bronze muscadine pomace extract combined with a liquid purple muscadine pomace extract to produce a liquid muscadine pomace extract, wherein a) the bronze muscadine pomace extract and the purple muscadine pomace extract are solvent extracted extracts, b) the mixture of bronze muscadine pomace extract and purple muscadine pomace extract promotes solubility of ellagic acid in the muscadine pomace extract, c) the bronze muscadine pomace extract and the purple muscadine pomace extract are filtered and fermented extracts, and d) the muscadine pomace extract has a polyphenol content of at least 2%. In additional embodiments, these topical compositions are used for reducing skin inflammation.

The foregoing and other objects, features, and advantages of the invention will become more apparent from the following detailed description, which proceeds with reference to the accompanying figures.

BRIEF DESCRIPTION OF THE DRAWINGS

FIG. 1 is a flow chart of an embodiment of the extraction method that lowers the condensed tannin content while substantially preserving polyphenol content.

FIG. 2 is schematic depiction of a system for carrying out the method of FIG. 1.

FIG. 4 is a table that summarizes the beneficial effects of the decolorized muscadine pomace extract as measured by the elastase, collagenase, 2,2-diphenyl-1-picrylhydrazyl (DPPH), TT dimer, keratinocyte viability, and tyrosinase tests.

DETAILED DESCRIPTION

I. Terms

Figure 3A:
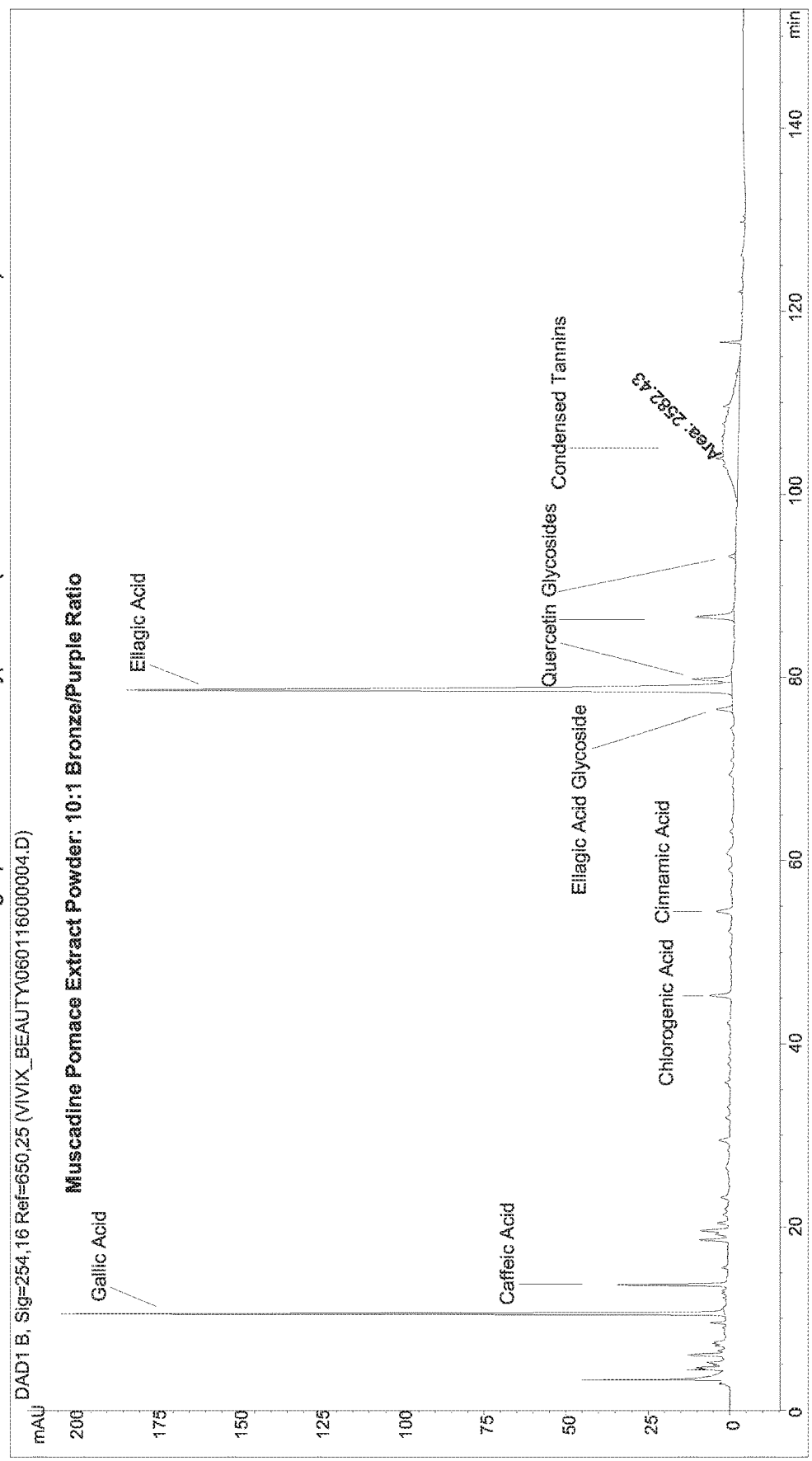
FIG. 3A and FIG. 3B are comparative traces of chromatographic profiles of polyphenols in a precursor muscadine pomace extract before (FIG. 3A) and the decolorized extract after (FIG. 3B) the tannin content is lowered using the methods disclosed herein. The desired polyphenolic profile of the precursor extract is retained, while the level of condensed tannins is greatly lowered in the decolorized extract.

The following explanations of terms and methods are provided to better describe the present disclosure and to guide those of ordinary skill in the art in the practice of the present disclosure. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. All percentages and ratios are calculated by weight unless otherwise indicated. The term "about" refers to an amount within a specific range of a value. For example, "about" a specific molecular weight or gram amount indicates within 5% of that molecular weight or gram amount. In a non-limiting example, "about" 100 grams refers to 95 grams to 105 grams. In addition, "about" a specific percentage refers to within 0.05%. In a non-limiting example, "about" 2% refers to 1.95% to 2.05%.

Administration: To provide or give a subject an agent by any effective route. Exemplary routes of administration include, but are not limited to, topical, oral, injection (such as subcutaneous, intramuscular, intradermal, intraperitoneal, intravenous, and intratumoral), sublingual, transdermal, intranasal, topical and inhalation routes.

Antioxidant composition: A composition that has antioxidant activity.

Antioxidative effective amount: An amount sufficient to induce an antioxidant effect in a subject to whom the amount of a composition is administered.

Chemokine: A chemotactic cytokine that mediates chemotaxis. Chemokines are small proteins (between 8 and 10 kDa) that can stimulate the recruitment of leukocytes to a site of inflammation. Inflammatory chemokines are induced by pro-inflammatory stimuli including IL-1 alpha and IL-6.

Cytokine: A group of proteins that are involved in cell signaling processes, including in the immune system. Cytokines include chemokines and interleukins, such as TNF alpha, IL-1 alpha, IL-1 beta, IL-3, IL-6, IL-7, IL-8, IL-10, IL-18, and IL-1RA.

Decolorized: A "decolorized" extract refers to one having less color than a reference, and it does not require an absence of coloration. A "decolorized" extract as used in this specification refers to the extract having a lowered level of condensed tannins and a lesser dark coloration of the type associated with condensed tannins in red grapes, red grape extracts, and red wine.

Effective Amount: An amount of a composition that alone, or together with an additional agent(s) (for example additional antioxidant(s) or additional anti-inflammatory compound(s)), induces the desired response. The effective amount can be administered in a single dose, or in several doses, for example daily. However, the effective amount can depend on the subject being treated, the type of the condition being treated, and the manner of administration.

Excipient: An inactive substance used as a carrier for the active ingredients of a composition. Excipients can include substances that are used to bulk up formulations with active ingredients, allow for convenient and accurate dosage, stabilize the active ingredients, and make the delivery system optically and/or organoleptically acceptable. Examples of pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like.

Extract: A solution or other preparation of at least some of the active ingredients of a plant or one or more of its parts, such as its fruit or seeds. The extracts disclosed herein are solvent extracts, in which seeds are exposed to a liquid extract solvent (such as heated water) to remove active principles from the seeds. An extract initially obtained by solvent extraction may be converted into a dried form and still be considered an "extract." An "aqueous" or "water" extract refers to an extract obtained by solvent extraction with water and no other solvent (such as ethanol).

Flavonoids: A class of plant secondary metabolites, on a dry weight basis, grape seeds contain about 4-8% flavonoids. Flavonoids constitute an important group of dietary polyphenolic compounds that are widely distributed in plants. More than 4000 chemically unique flavonoids have been identified in plant sources, such as fruits, vegetables, legumes, nuts, seeds, herbs, spices, flowers, as well as in beverages such as tea, cocoa, beer, wine, and grape juice.

Flavonoids in grape seeds refer primarily to flavan-3-ols, specifically (+)-catechin, (−)-epicatechin, and (−)-epicatechin 3-gallate, and complexes thereof. The flavan-3-ols in grape seeds are present in monomeric, oligomeric or polymeric forms. Two or more chemically linked flavan-3-ol monomers are called proanthocyanidins or oligomeric proanthocyanidins ("OPCs"), which includes procyanidins and prodelphinidins. OPCs containing two monomers are called dimers, three monomers are called trimers, four monomers are called tetramers, five monomers are called pentamers, etc. The oligomers have chain lengths of 2 to 10; polymers represent components with chain lengths greater than 10. Thus, oligomers in grape extracts include, for instance, dimers and trimers, and there is evidence that the polymers can have as many as 50-100 units.

Flavonoids are present in all parts of the grape, including the skin, juice and pulp, and not just in the grape seed. In order for polyphenolic compounds to be used commercially as a grape extract, including as grape seed or grape pomace extracts, these compounds have to be separated from grapes in a more concentrated form. Scientific studies have shown that the antioxidant power of proanthocyanidins is 20 times greater than vitamin E and 50 times greater than vitamin C. Extensive research suggests that grape seed extract is beneficial in many areas of health because of its antioxidant effect to bond with collagen, promoting youthful skin, cell health, elasticity, and flexibility. Other studies have shown that proanthocyanidins help to protect the body from sun damage, to improve vision, to improve flexibility in joints, arteries, and body tissues such as the heart, and to improve blood circulation by strengthening capillaries, arteries, and veins.

Inflammation: A localized biological reaction that can produce redness, swelling and pain as a result of damaging stimuli including infection, irritation or injury. Inflammation can be chronic or acute, and may be pathogenic. Immune cells initiate the inflammatory response, and release inflammatory mediators responsible for increased blood flow and leakage of plasma fluid into the damaged tissue. Inflammatory mediators whose presence is indicative of inflammation include IL 1-alpha, IL-6 and PGE2.

Interleukin: A cytokine that can mediate inflammatory reactions. There are multiple families of interleukins (IL). Interleukin 1 (IL-1) is a family of interleukins with at least eleven members, including IL-1 alpha. IL-1 alpha is generally responsible for the production of inflammation, and is produced by epithelial cells. Interleukin 6 (IL-6) is a cytokine that can stimulate the immune response and is secreted after cellular trauma such as burns or other tissue damage. IL-6 can initiate synthesis of PGE2 when acting as a pro-inflammatory mediator.

Muscadine Grape (*Vitus rotundifolia*): Grapes native to the southeastern United States, and found in the wild from Delaware to the Gulf of Mexico and westward to Missouri, Kansas, Oklahoma, and Texas. Muscadines are well adapted to the warm, humid conditions of the southeastern United States. The fruit is borne in small, loose clusters of 3-40 grapes, quite unlike the large, tight bunches characteristic of European and American grapes. The round, 1 to 1½ inch fruits have a thick, tough skin and contain up to 5 hard, oblong seeds. In color the fruits range from greenish bronze through bronze, pinkish red, purple and almost black. They are considered a red grape as the term is used in this specification.

Many different varieties of muscadine grapes are available, including female (pistillate) varieties such as Black Beauty, Black Fry, Darlene, Fry, Higgins, Jumbo, Scuppernong, Sugargate, Summit, Supreme, and Sweet Jenny, and self-fertile varieties such as Carlos, Cowart, Dixieland, Dixie Red, Fry Seedless, Magnolia, Nesbitt, Noble, Redgate, Regale and Sterling.

For example the bronze colored varieties of muscadine grapes are identified by those skilled in the art as including Carlos, Chowan, Doreen, Higgins, Magnolia, Nevermiss, Pamlico, Roanoke, Scuppernong, Sterling, and Summit cultivars. Purple varieties are darker skinned then the bronze colored varieties and include Albermarle, Bountiful, Cowart, GA-1, Hunt, NC-1, Noble, Regale, Tarheel, and Jumbo. Some of the purple varieties are also referred to as Black colored.

The phytochemical constituents of the whole muscadine grape differ from *Vitis vinifera*. Muscadines have a higher total phenolic content distinguished by high ellagic, gallic, and flavonoid glycoside concentrations. The presence of ellagic acid in muscadine grapes is unique and is found in the form of free ellagic acid, ellagic acid glycosides, methoxylated derivatives and ellagitannins. Another unique feature is the anthocyanin chemistries observed in muscadines. Present as 3,5-diglucosides (as opposed to 3-glucosides) of delphinidin, cyanidin, petunidin, peonidin, and malvidin in non-acylated forms, these compounds and the natural color influence from other anthocyanins present within the grape impart a dark purple color to juice and pomace obtained from the purple varieties. Purple pomace extracts contain anthocyanins while bronze pomace extracts do not.

The red and purple colored anthocyanins found in bronze and purple muscadine grapes are polyphenolic compounds that have antioxidant properties. Purple and bronze muscadine grapes contain several other flavonoid classes of polyphenols with flavan-3-ols and their oligomers being the most abundant class and flavonols being the second most abundant flavonoids present in whole muscadines. The major phenolics reported for the muscadine skin fraction (in descending order) are ellagic acid, myricetin, quercetin, and kaempferol while those reported for seeds are epicatechin, catechin and gallic acid (Pastrana-Bonilla et al. *J. Agric. Food Chem.* 51:5497-5503, 2003).

A muscadine grape contains pomace and juice. "Other than the whole grape" includes a muscadine grape from which at least some of the juice has been extracted, and in some examples includes less than 95% or 90% of the original juice in the grape.

Pharmaceutically Acceptable Vehicles: The pharmaceutically acceptable vehicles (carriers) useful in this disclosure are conventional. *Remington's Pharmaceutical Sciences*, by E. W. Martin, Mack Publishing Co., Easton, Pa., 19th Edition (1995), describes compositions and formulations suitable for pharmaceutical delivery of one or more compositions, such as one or more grape extract compositions, such as grape seed extract compositions, and additional naturally or non-naturally occurring pharmaceutical agents that would not be found with the grape extracts in nature. The use of pharmaceutically acceptable carriers does not imply that that product so made is useful only for pharmaceutical purposes. Rather it implies that the product is suitable for administration to or consumption by a subject, for example topical composition. In particular embodiments, the vehicle is a carrier for a topical composition, such as a liquid, gel, foam, cream, ointment or lotion. Particularly useful vehicles are those that are pharmaceutically or cosmetically acceptable for topical applications, such as one or more aqueous systems, glycerin, $C_{1-4}$ alcohols, fatty alcohols, fatty ethers, fatty esters, polyols, glycols, vegetable oils, mineral oils, liposomes, laminar lipid materials, silicone oils, water, or any combinations thereof.

For topical compositions, such as those disclosed herein, the muscadine grape extract compositions can be formulated in any suitable product form. Such product forms include, but are not limited to, aerosol spray, cream, dispersion, emulsion, foam, gel, liquid, lotion, mousse, ointment, patch, pomade, powder, pump spray, solid, solution, stick, or towelette. The carrier can also be a variety of existing skin lotions, gels, creams, ointments, toners, cleansers, moisturizers or sun screens to which the muscadine grape extract is added in a desired concentration, for example 0.025%-0.25% by weight.

Polyphenols: Polyphenols from grapes and cocoa have been found to enhance both cardiovascular function and cognitive health. Flavanols (also called flavan-3-ols) represent the majority of grape seed and cocoa polyphenols; this class of phenolic compounds ranges from monomeric species such as catechin and epicatechin to oligomers (often termed proanthocyanidins) to polymers (often termed tannins or condensed tannins). The term "phenolic" is used interchangeably with the term polyphenol in the art and in this specification.

Polyphenols are also present in other parts of the grape, including in the skin, juice and pulp. The highest concentration of polyphenols in a grape resides in the grape seeds. Grape seeds are waste products of the winery and grape juice industry. These seeds contain lipid, protein, carbohydrates, and 4-8% polyphenols (dry weight) depending on the variety. Grape seed extract is therefore a powerful antioxidant that protects the body from premature aging, disease, and degeneration.

Pomace: The skins, seeds, and pulp remaining following juice extraction. In one example, a pomace extract is a bronze muscadine pomace extract, a purple muscadine pomace extract or a combination thereof. Many different varieties of muscadine grape pomaces are available as starting materials, and they include female (pistillate) varieties such as Black Beauty, Black Fry, Darlene, Fry, Higgins, Jumbo, Scuppernong, Sugargate, Summit, Supreme, and Sweet Jenny, and self-fertile varieties such as Carlos, Cowart, Dixieland, Dixie Red, Fry Seedless, Magnolia, Nesbitt, Noble, Redgate, Regale and Sterling. Muscadine pomace contains phenolic compounds, including gallic acid and ellagic acid, having antioxidant properties.

The pomace can be present in a whole grape wherein the whole grape contains at least 90% or 95% of the juice of the grape, or the pomace can be substantially isolated and consist essentially only of the pomace once the grape has been compressed to remove the juice.

Pomace-only: The pomace portion of a grape from which juice has been removed, for example by compression of the grape. As used herein, "pomace-only" refers to a pomace that contains no more than 1% juice as a percentage of its weight. In some embodiments the pomace-only contains no more than 0.5% juice as a percentage of its weight.

Prostaglandin: A biologically active lipid containing 20 carbon atoms, including a pentane ring. Prostaglandins are involved with mediating inflammation, and prostaglandin E2 (PGE2) is produced from arachidonic acid via cyclooxygenases and prostaglandin E synthases. Levels of cyclooxygenases are increased in injured and/or inflamed cells, which results in increased PGE2 production.

Purified: The term purified does not require absolute purity; rather, it is intended as a relative term. Thus, for example, a purified substance is one in which the substance is more enriched than the substance in its natural environment, for example in a fruit (e.g., grape). In one embodiment, a preparation is purified such that the substance represents at least about 5% (such as, but not limited to, at least about 10%, about 20%, about 30%, about 40%, about 50%, about 70%, about 80%, about 90%, about 95%, about 98% or about 99%) of the total content of the preparation.

Range: With respect to ranges, the term "in the range of x to y" or "from x to y" includes any value between x and y, as well as the endpoints x and y.

Red grapes: Red grapes are those from which red wine is generally made, and which have generally higher levels of tannins than white grapes from which white wine is made. "Red wine" is a general term for dark wines. A determination of the color of a wine can be made according to the International Organization of Vine and Wine which provides method to assess the color of a wine using a spectrophotometer and the calculation of indices in the Lab color space. Examples of grapes from which red wine is made include Syrah, Merlot, Cabernet Sauvignon, Malbec, Pinot Noir, Zinfandel, Sangiovese, Barbera, and Muscadine. Muscadine grapes (*Vitus rotundifolia*) range in color from bronze to dark purple to black in color when ripe.

Selective extraction: Selective extraction refers to preferential extraction of a target (such as condensed tannins). In some embodiments, selective extraction means that the target is the predominant species extracted.

Skin care composition: A topical composition having active ingredients that can improve the health, aesthetic and/or cosmetic appearance of skin, Such improvements can be manifested, for example, by a reduction in the level of markers of inflammation, or a reduction in dermatological signs of aging caused by factors such as chronological aging, hormonal aging, and photoaging; reduction in skin fragility, pore size reduction, loss of collagen and/or elastin; diminishing appearance and/or depth of lines and/or wrinkles including fine lines and/or wrinkles; reducing hyperpigmentation; improvement in skin tone, radiance, clarity and/or tautness; reducing skin sagging; promoting antioxidant activity; improving skin firmness, plumpness, texture, suppleness and/or softness; improvement in procollagen and/or collagen production.

Subject: Living multi-cellular vertebrate organisms, a category that includes both human and veterinary subjects, such as a companion animal, including a cat, dog or horse. A "subject in need of an increase in mitochondrial biogenesis and/or antioxidant activity" is a subject who may benefit from such an increase, such as a subject who desires to decrease signs of age, offset tissue damage caused by oxidation, and/or improve cardiovascular, neurological, tumor-related, skin-appearance or other conditions that are associated with oxidative stress. A "subject in need of a reduction in inflammation" is a subject who may benefit from such a reduction, such as a subject who desires to offset tissue damage caused by inflammation such as UV radiation, or decrease signs of aging, skin-appearance or other conditions that are associated with skin inflammation. As used herein, a "healthy subject" does not have any major underlying medical inflammatory condition, including but not limited to, eczema, cardiovascular disease or psoriasis.

Tannins: Naturally occurring polyphenolic biomolecules that bind to and precipitate proteins, amino acids and alkaloids. The term "tannin" originally referred to the use of wood tanning agents from oak that were used in tanning animal hides into leather. However, the term tannin is widely applied to a large polyphenolic compounds with molecular weights ranging from 500 to over 3,000 (gallic acid esters) and up to 20,000 (proanthocyanidins) that are found in plants, such as red grape seeds, seed and stems. In terms of their chemical composition, plant tannins are divided into the hydrolyzable tannins and the condensed tannins or flavonoids. The hydrolyzable tannins are polymerized simple phenolic substances, such as esters of gallic acid and its dimers (digallic acid, ellagic acid). The hydrolyzable tannin can be further divided into gallotannins that yield gallic acid after hydrolysis, and ellagitannins that release ellagic acid after hydrolysis. In contrast to the hydrolyzable tannins, the condensed tannins are not decomposable by hydrolysis. On the contrary, when subjected to heating in an acidic medium they progressively polymerize and form amorphous anthocyanin pigments of red color, or insoluble yellow-brown products, of high molecular mass, called phlobaphenes.

Topical application: A topically applied agent is applied only in a specific surface area of the skin, and not throughout the body. In particular examples the composition is applied to the skin or the eye in an area where an effect is desired, such as the reduction of fine lines or wrinkles, or is applied to the skin in an area where an anti-inflammatory effect is desired, such as areas that are exposed to UV radiation. For example, the composition can be applied in a topical preparation to facial skin. A topical composition that is intended for application to the skin is a "skin composition."

Ultrafiltration: A type of membrane filtration in which forces (such as pressure or concentration gradients) lead to a separation through a semipermeable membrane. Ultrafiltration membranes are typically characterized by the molecular weight cut off (MWCO) of the membrane. Suspended solids and solutes of higher molecular weight are retained in the retentate, while water and lower molecular weight solutes pass through the membrane in the permeate. Different types of modules can be used for ultrafiltration processes. Examples of such modules are tubular elements that use polymeric membranes cast on the inside of plastic or paper tubes; hollow fiber designs that contain multiple hollow fibers; spiral wound modules in which flat membrane sheets are separated by a thin meshed spacer material that is rolled around a central perforated tube and fitted into a tubular steel pressure vessel casing; and plate and frame assemblies that use a membrane placed on a flat plate separated by a mesh like material through which the filtrate passes.

Unit dose: A physically discrete unit containing a predetermined quantity of an active material calculated to individually or collectively produce a desired effect, such as a therapeutic effect. A single unit dose or a plurality of unit doses can be used to provide the desired effect or activity, such as antioxidant activity or reduction in inflammation. In one example, a unit dose includes a desired amount of an agent that promotes cardiovascular or cognitive health. In an additional example, a unit dose includes a desired amount of an agent that reduces skin inflammation. In another example, the unit dosage form contains multiple predetermined dosages of the active material.

II. Description of Several Embodiments

A. Obtaining Muscadine Grape Pomace Extract Precursor Material for Subsequent Decolorization The disclosed compositions and methods can be used to lower the condensed tannin content of a variety of plant extracts that include tannins. Tannins are widely distributed in many types of plants. Tannins can be found in leaf, bud, seed, root and stem tissues. Tannins are found in monocots (44 families, according to Wikipedia) and dicots (180 families, according to Wikipedia), and are found in gymnosperms and angiosperms. All species of the following dicots contain tannins: Aceraceae, Actinidiaceae, Anacardiaceae, Bixaceae, Burseraceae, Combretaceae, Dipterocarpaceae, Ericaceae, Grossulariaceae, Myricaceae. All species of Najadaceae and Typhaceae (monocots), also contain tannins. Condensed tannins (incluidng proanthocyanidins, polyflavonoid tannins, catechol-type tannins, pyrocatecollic type tannins, non-hydrolyzable tannins or flavolans) are found in plant species such as *Ltihcarpus glaber, Prunus* sp, *Schinopsis lorentzil, Acacia mollissima, Vitis vinifera*, and *Commiphora angioensis*. Pine barks and spruce barks contain condensed tannins. Vascular plants (e.g., *Tracheophytes*, vascular plants) also include condensed tannins. The disclosed methods are of use to lower the condensed tannin content of extracts of any of these plants that contain condensed tannins.

In some embodiments, the plant extracts are grape pomace extracts, such as, but not limited to, muscadine grape pomace extracts that contain condensed tannins. In some non-limiting examples, the plant extracts are red grape pomace extracts that contain condensed tannins. For purposes of illustration only, the methods and compositions are described with reference to a muscadine grape pomace extract that would be the precursor material prior to decolorization. In this specific example, the muscadine pomace extract is a combined extract of bronze and purple muscadine grapes that have an enhanced solubility of ellagic acid (which is unique to muscadine grapes). As disclosed in PCT Publication No. WO 2010/014870 and PCT Publication No. WO 2010/014873 and U.S. Pat. Nos. 8,568,804, 9,132,162 and 9,173,916 (all five of which are incorporated herein by reference), muscadine extracts with improved ellagic acid solubility can be obtained by combining bronze and purple muscadine pomace extracts. Various methods of making the combined extracts were disclosed, such as combining a bronze muscadine pomace extract with a purple muscadine pomace extract to produce a muscadine pomace extract, wherein the ratio of bronze muscadine pomace extract to purple muscadine pomace extract ranges from 0.1 to 10 (weight to weight), such as 0.3 to 3 (weight to weight). The combined extract could be made by separate extraction of bronze and purple muscadine grapes with subsequent combination of the extracts, or by simultaneous extraction of bronze and purple muscadine grapes combined in desired ratios. In the disclosed examples, the precursor extract is an aqueous extract of the muscadine pomace.

The applicant's incorporated PCT Publication No. WO 2010/014870, PCT Publication No. WO 2010/01487, U.S. Pat. Nos. 8,568,804, 9,132,162 and 9,173,916 disclose that the precursor muscadine pomace extract compositions have improved antioxidant activity. Methods of producing the disclosed compositions include combining a muscadine (*Vitis rotundifolia*) pomace extract having a polyphenol content of at least 2% and trans-resveratrol from a source other than muscadine with a minimum purity of at least 5%, wherein a ratio of muscadine polyphenols to trans-resveratrol is in the range of 0.1/1 to 10/1 (weight to weight). Methods of producing the disclosed compositions include combining a muscadine (*Vitis rotundifolia*) pomace extract having a polyphenol content of at least 2% and trans-resveratrol from a source other than muscadine with a minimum purity of at least 5%, wherein a ratio of muscadine pomace extract to trans-resveratrol is in the range of 0.2/1 to 50/1 (weight to weight), such as 5/1 to 50/1 (weight to weight) including 20/1 to 50/1 (weight to weight), such as 18 to 1 (weight to weight), thereby producing a muscadine pomace extract and trans-resveratrol mixture with antioxidant activity.

In some embodiments, the ratio of bronze to purple muscadine pomace precursor extract ranges from 0.1 to 10, such as 0.3 to 3. For example, the ratio of bronze muscadine pomace extract to purple muscadine pomace extract is about 2.75 to about 1 (weight to weight), 2.5 to about 1 (weight to weight), about 2.25 to about 1 (weight to weight), about 2 to about 1 (weight to weight), about 1.5 to about 1 (weight to weight), or about 1 to about 1 (weight to weight). In other examples, the ratio is about 10 to about 1, about 7.5 to about 1, or about 5 to about 1. As used herein the term "about" is defined as ±0.5. In a particular example, the ratio of bronze muscadine pomace extract to purple muscadine pomace extract is about 2.25 to about 1 (weight to weight). In certain embodiments, the muscadine (*Vitis rotundifolia*) pomace precursor extract has a polyphenol content of at least 2%. For example, the polyphenol content is at least 3%, at least 3.5%, at least 4%, at least 4.5%, at least 5%, at least 6%, at least 8%, at least 10%, at least 12%, or at least 14%. In a particular example, the muscadine (*Vitis rotundifolia*) pomace extract has a polyphenol content of about 4%.

In some embodiments, the disclosed muscadine pomace precursor extracts include 20% to 50% solids, such as at least 25%, at least 30%, at least 35%, at least 37%, at least 40%, at least 42%, at least 44%, at least 46% or at least 48%, in a liquid. In a particular example, the extract includes about 40% solids in a liquid.

The precursor extracts can be obtained by any extraction method, such as pressing under pressure or extracting with a solvent. Particular examples are solvent extraction, for example with alcohol, water (such as heated water), or a combination of alcohol and water. The extract can further be fermented to remove extracted sugars. In one example, fermentation is performed following extracting the bronze muscadine pomace and purple muscadine pomace but prior to combining the bronze muscadine pomace extract with the purple muscadine pomace extract to produce a disclosed muscadine pomace extract. In other examples, fermentation is performed after combining the bronze muscadine pomace extract with purple muscadine pomace extract in the desired post extraction ratio (such as, but not limited to, at about a 2:25 to 1 bronze to purple ratio).

Fermentation may be performed by any method known to one of skill in art. For example, yeast and yeast nutrients can be added to the pomace and fermentation continued until the residual sugar content is converted to ethanol. In one example, two pounds of yeast are added per 1000 gallons of 1× (unconcentrated) extract; fermentation is typically complete after three days. In other examples, the amount and/or strain of yeast and duration and temperature of fermentation may vary according to individual methods known to one of skill in art. In some examples, enzymes are used to clarify and/or settle residues or to improve extraction yield in the pomace extracts. Examples of such enzymes include pectinase or a blend of enzymes from *Aspergillus niger* that are commercially available from sources such as Scott Laboratories. These enzymes may be added to the pomace extract before or during fermentation.

In some embodiments, the bronze muscadine pomace extracts and purple muscadine pomace extracts are filtered prior to and/or following fermentation. Filtration can be performed according to general methods known to those of skill in the art. In a particular example, extracts are filtered through sieves of appropriate mesh size, such as USP mesh (typically 120 mesh) or a similar cloth filter (for example filters commercially available from Millipore Corporation).

In certain embodiments, methods of making muscadine pomace precursor extracts further include concentrating the bronze muscadine pomace extract and the purple muscadine pomace extract so that each extract includes 20% to 50% solids, such as at least 25%, at least 30%, at least 35%, at least 37%, at least 40%, at least 42%, at least 44%, at least 46% or at least 48%, in a liquid. In a particular example, the extracts are concentrated so that each extract includes about 40% solids in a liquid. Generally known methods for concentrating samples, including methods for concentrating samples disclosed herein, can be used to concentrate the bronze and purple extracts.

In any of the foregoing examples of extraction methods, whole purple grapes can be substituted for purple pomace. The purple muscadine pomace extract can include (a) an extract of whole purple muscadine grapes; (b) an extract of purple muscadine pomace from other than whole grapes; or (c) a mixture of (a) and (b). The whole purple grapes contain grape juice that is a source of anthocyanins from other than the grape pomace, and when solvent extracted from the whole grape these anthocyanins have now been found to surprisingly enhance solubility of ellagic acid in the mixture of bronze and purple muscadine grape extracts. However, additional sources of anthocyanins can also be provided by a colored fruit or a byproduct of a colored fruit other than purple muscadine grapes, such as a blueberry, blackberry or raspberry. In other examples, the anthocyanin is from a product of a fruit processing stream such as a juice concentrate or a byproduct of a fruit processing stream such as fruit skins that are separated from a fruit puree processing stream.

The muscadine grape pomace precursor extract obtained by any of these methods has levels of condensed tannins that impart dark coloration to the extract. The precursor extract can therefore be further processed as described below to reduce the tannin content and produce a decolorized extract.

B. Reducing Tannin Content of the Extract to Make a Decolorized Extract

Once the precursor extract is obtained, it is subjected to the decolorization process. An example of a decolorization process for reducing the tannin content of the muscadine grape pomace extract is shown in FIG. 1. A precursor material is a muscadine pomace extract liquid concentrate 1. In this example, the concentrate 1 is 40-45% solids, as described in U.S. Pat. Nos. 8,512,771 and 9,173,916. Concentrate 1 is diluted to less than 10% solids by adding purified water to produce an 8% solids solution 2 (the percent solids can range from 2-10%). Solution 2 is heated to 130-135° F., and passed through a microfiltration device 3 to clarify the material. The microfiltration process is more efficient when the precursor material is diluted to a very low level of solids (2-5%) and heating also helps facilitate the process. In this specific example, the microfiltration device 3 is a mechanical filter of 0.45 micron pore size and NMWCO of 200,000 daltons (or 200 kDa) which removes microorganisms and suspended particles from solution in preparation for a subsequent ultrafiltration treatment 4. The clarified extract is quickly cooled down to <50° F. in a holding tank before starting the $1^{st}$ stage ultrafiltration step.

The cooled and clarified extract is then subjected to ultrafiltration treatment 4 with standard nominal molecular weight cutoff ultrafiltration membrane of 1000 daltons (or 1 kDa) yielding a permeate (Fraction A) at 5. Fraction A includes compounds having molecular weights of less than 1000 and contains mainly organic acids, sugars, and minerals but surprisingly contains less than 1% phenolic compounds. These phenolic compounds include trace amounts of phenolic acids and flavonoids such as gallic acid and quercetin. Although molecules having a molecular weight of up to 1,000 daltons are able to permeate the ultrafiltration membrane, it was unexpectedly found that this fraction contained a very low phenolic acid content, perhaps due to physicochemical interactions between the phenolic acids and other molecules, possibly fiber, contained in the precursor material. This unexpected finding can be obtained with the use of standard nominal molecular weight cutoff ultrafiltration membranes as low as 500 daltons and up to 5000 (or 5 kDa). Fraction A could serve as a "muscadine" type flavor component in other products, but this material is discarded in the process of preparing the skin care extract.

The retentate (material that does not pass through the ultrafiltration membrane) remaining from the low molecular weight ultrafiltration (described above) is reconstituted in purified water to approximately 2% solids concentration and subjected to a second ultrafiltration process 6 with a 30 kDa cutoff ultrafiltration membrane. The resulting retentate 7 (Fraction C) is discarded and the permeate 8 (Fraction B) containing the decolorized muscadine pomace extract is retained for further processing into a skin care composition. Fraction C primarily contains polymerized condensed tannins, protein, and fiber. In contrast, Fraction B is enriched with polyphenols (9-10% dry weight), low in sugars (<4% dry weight) and greatly reduced in polymeric condensed tannin content (undergoing a minimum reduction of 70% of the initial condensed tannin content). Although molecules having a molecular weight of up to 30,000 daltons are able to permeate the ultrafiltration membrane, it was unexpectedly found that at least 70% of the polymeric condensed tannins remained in Fraction C, possibly owing to physicochemical interactions. This unexpected finding may result from the use of standard nominal molecular weight cutoff ultrafiltration membranes as low as 25,000 daltons (25 kDa) and up to 100,000 daltons (or 100 kDa).

Fraction B also contains fiber (about 1.0%), protein (about 7.8%), fat (about 0.1%) and organic acids (about 16.0%). Fraction C, which is enriched in polymeric condensed tannins, could serve as a source of antioxidants for use in a variety of products, but this material is discarded in the preparation process of the skin care extract. At this point in the decolorization process, the muscadine fruit extract, Fraction B, has minimal sugar content (<4% dry weight) and is greatly reduced in polymeric condensed tannins. Fraction B is ideal for use in skin care products because it contains powerful polyphenol antioxidants yet has little or no potential for brown discoloration owing to the removal of condensed tannins and its minimal sugar content. When introduced into various formulations for topical use, brown color undertones are not detected.

Permeate 8 (Fraction B) is further processed by treating it with activated carbon at a 0.3% weight to weight basis to remove odiferous components that are undesirable in a skin care product (buttery/yeasty notes). After treatment with activated carbon, Fraction B is subjected to a final microfiltration process 9 to remove all traces of activated carbon. After microfiltration the solution is concentrated 10 to 30-40% solids before mineralization with magnesium oxide to facilitate a free flowing powder after drying. Magnesium oxide is added in at an input of 7.0% on a dry weight basis to the concentrate to completely facilitate the mineralization process, so as to form the magnesium salts of all the organic acids that exist in the extract. Finally, the product is subjected to drying/milling 11 to provide a uniform particle size. Silicon dioxide is added during this milling stage to prevent product caking.

Compared to the precursor material, Fraction B has a mass reduction of 75-80% yet only 35-40% polyphenol content reduction when subjected to the above described process. Therefore, when comparing Fraction B to the precursor material, on an equivalent mass basis, the resulting reduction of nontannic polyphenol content in Fraction B is only 18-20%. Thus, the predominant loss of polyphenols in Fraction B is attributed to the chemical class of polymeric condensed tannins; virtually no loss of other polyphenol chemical classes was detected (see chromatograms in FIGS. 3A and 3B). Thus, Fraction B contains, on average, 9% muscadine polyphenols (predominantly nontannic) whereas, the precursor material contains, on average, 14% polyphenols consisting of both tannic and nontannic muscadine polyphenols. Tables 1-3 depict the nutritional and polyphenol content comparisons and FIG. 3A and FIG. 3B provide a chromatographic comparison, for precursor material versus the decolorized extract produced by the above described process.

Table 1 compares the nutritional profiles (presented as % of dry extract) of the precursor and decolorized extracts. While the nutritional profiles are quite similar; owing to the mass reduction of the precursor material, there is some concentration of nutrient classes such as protein and simple sugars. Nevertheless, the final simple sugar (monosaccharide) content of the decolorized extract is quite low (<4-5%)

and thus suitable for use in a topically applied product. Table 2 shows, on a dry weight basis, the total polyphenol content of each extract and further divides the polyphenol content into condensed tannin content and content of polyphenols other than condensed tannins. As shown in Table 2, while the total polyphenol content is about 35% lower in the decolorized extract (90 versus 140 mg/g dry weight), the condensed tannin content of the decolorized extract is at least 70% lower than that found in the precursor extract (6 versus 21 mg/g dry weight). Thus, the majority (roughly 80%) of the polyphenol loss is attributable to the removal of condensed tannins confirming the preferential removal of condensed tannins versus other polyphenols using the process described above.

Figure 3B:

The decolorized extract retains all the core polyphenols (listed in Table 4) found in the precursor material (phenolic acids, flavonoids, anthocyanins, and hydrolyzable tannins) as shown in the chromatograms in FIGS. 3A and 3B, and further illustrated in Table 3 wherein the core/hallmark muscadine polyphenols are profiled. Using analytical methods, approximately 30% of the total polyphenols in the precursor extract (43.84 mg out of 140 mg) were measured as single phenolic classes and/or compounds and were compared to the corresponding classes/compounds in the decolorized extract. As shown in Table 3, important (and in some cases unique) muscadine polyphenol classes such as phenolic acids, ellagic acid, gallic acid, ellagitannins, and gallotannins were detectable in the decolorized extract; in some cases, the percentage of selected compounds, e.g., gallic acid, increased. Thus, the primary difference in polyphenol content between the two extracts is the 70% reduction in condensed tannin content. In summary, the reduction of condensed tannin content together with the low level of simple sugars renders decolorized Fraction B to be amenable for skin care applications when added in the typical usage amounts of topical formulations. These formulations are of use for skin care (see below), and are more stable when stored, so that the product does not turn brown or darken in color over time.

The disclosed extraction method for selectively lowering the levels of condensed tannins surprisingly and advantageously preserves or improves the levels of other polyphenols that are beneficial in treatment of the skin, while avoiding the drawbacks posed by the presence of high levels of condensed tannins.

TABLE 1

Nutritional Profiles of Precursor and Decolorized Muscadine Extracts

| Compound Class | Precursor Extract (% dry weight) | Decolorized Extract (% dry weight) |
|---|---|---|
| Protein | 4.6 | 7.8 |
| Fat | 1.0 | 0.1 |
| Ash (Inorganic Constituents) | 16.0 | 18.9 |
| Sugar Acids | 16.5 | 16.5 |
| Soluble Fiber | 0.0 | 0.9 |
| Insoluble Fiber | 2.0 | 0.1 |
| Organic Acids | 23.0 | 16.0 |
| Sugar Alcohols | 3.9 | 8.8 |
| Polyphenols | 14 (Avg. G.A.E.) | 9 (Avg. G.A.E.) |
| Simple Sugars | 0.5 | 3.5 |
| Moisture | 12.0 | 10.0 |
| Amino Acids | 3.9 | 7.8 |
| "other" | 2.6 | 0.6 |
| Total | 100.0 | 100.0 |

TABLE 2

Polyphenol content of Precursor and Decolorized Muscadine Extracts Phenolic Profiling

| Phenolic Class | Precursor (mg/g extract) | Precursor (% of total polyphenols) | Decolorized (mg/g extract) | Decolorized (% of total polyphenols) | Analysis Method |
|---|---|---|---|---|---|
| All other Polyphenols | 119.0 | 85.0 | 84.0 | 93.3 | (G.A.E. minus condensed tannins)* |
| Condensed Tannins | 21.0 | 15.0 | 6.0 | 6.7 | n-Butanol-HCL assay |
| Total Polyphenols | 140 | 100 | 90 | 100 | G.A.E Assay |

*Gallic Acid Equivalents assay (Total Polyphenols via UV/VIS) - Condensed Tannins assay via UV/VIS = non-condensed tannins content.

TABLE 3

Polyphenol Profiles of Precursor and Decolorized Muscadine Extracts

| Phenolic Class | Precursor (mg/g extract) | Precursor (% of identified polyphenols) | Decolorized (mg/g extract) | Decolorized (% of identified polyphenols) | Analysis Method |
|---|---|---|---|---|---|
| Ellagic Acid | 2.78 | 6.3 | 0.56 | 2.6 | HPLC/MS Quantitation w/Respective Standards |
| Ellagic Acid Glycosides | 0.68 | 1.6 | 0.67 | 3.1 | |
| Gallic Acid | 7.58 | 17.3 | 6.55 | 30.7 | |
| Quercetin/Glycosides | 1.35 | 3.1 | 0.55 | 2.6 | |
| Gallotannins | 2.21 | 5.1 | 2.16 | 10.1 | Hydrochloric Acid Hydrolysis HPLC/MS |
| Ellagitannins | 2.60 | 5.9 | 1.64 | 7.7 | |

TABLE 3-continued

Polyphenol Profiles of Precursor and Decolorized Muscadine Extracts

| Phenolic Class | Precursor (mg/g extract) | Precursor (% of identified polyphenols) | Decolorized (mg/g extract) | Decolorized (% of identified polyphenols) | Analysis Method |
|---|---|---|---|---|---|
| | | | | | Quantitation: Ellagic Acid and Methyl Gallate increase |
| Proanthocyanidins (Oligomeric/Polymeric) | 20.83 | 47.5 | 6.33 | 29.7 | C-18 S.P.E. Vanillin-Sulfuric Acid Assay & n-Butanol-HCL assay |
| Anthocyanins | 3.34 | 7.6 | 0.99 | 4.6 | HPLC/MS Quantitation (520 nm) Cyanidin-3,5-Diglucoside Std |
| Catechins | 0.59 | 1.3 | 0.60 | 2.8 | HPLC/MS Quantitation (280 nm) (+/−)-Catechin Std |
| Phenolic Acids | 1.88 | 4.3 | 1.29 | 6.1 | HPLC/MS Quantitation (254 nm) Chlorogenic Acid |
| Experimental Total | 43.84 | 100 | 21.34 | 100 | |

TABLE 4

Core Muscadine Grape Polyphenols

Phenolic Acids

Ellagic Acid (aglycone & glycosides)
Gallic Acid
Chlorogenic, Caffeic, Cinnamic, and p-Coumaric Flavonoids Anthocyanosides: diglycoside linkages
Anthocyanidins: delphnidin, petunidin, malvidin
Flavonols: quercitin, myricetin, and kaempferol
Flavanols (flavan-3-ol's): catechin, epicatechin
Stilbenes trans-Resveratrol, piceatannol(tetrahydroxy)

Tannins

Hydrolyzable: ellagitannins, gallotannins
Condensed: proanthocyanidins (oligomeric/polymeric)

C. Skin Products

The decolorized muscadine pomace extract having the reduced content of condensed tannins can be incorporated into a variety of skin care products, such as a gel oil cleanser, retinol serum concentrate, a day moisturizer with sun screen, clarifying treatment toner pads, and facial skin renewal cream. The muscadine pomace extract can be 0.00001% to 1% by weight of the skin care composition, such as 0.0001% to 1% by weight of the skin care composition, 0.001% to 1% by weight of the skin care composition, or 0.01% to 1% by weight of the skin care composition. In some embodiments, the muscadine pomace extract is for example 0.025% to 1%, such as 0.025 to 0.25%, by weight of the skin care composition. In other embodiments, the muscadine pomace extract is, for example, 0.0004% to 0.4% by weight of the composition. The resulting skin care composition has a polyphenol profile that is beneficial to the skin, but the product is relatively decolorized because of its lower condensed tannin content. As used herein, a "low condensed tannin content" means a condensed tannin content of 10% or less by weight.

The disclosed methods for preparing a decolorized muscadine pomace extract that has a lower level of condensed tannin content as compared to a muscadine pomace extract that has not been decolorized, can be used for topical skin compositions and methods of treating inflammation as described in sections C and D. Any of the methods disclosed in sections A and B can be used to prepare compositions formulated for administration to the skin.

1. Bioassays Demonstrate Beneficial Effect of Muscadine Pomace Extract on Skin

Various bioassays have demonstrated the mode of action of the muscadine pomace extract on the skin. The beneficial effects of the muscadine pomace extract skin care composition containing the decolorized extract are summarized in FIG. 4 for the elastase, collagenase, DPPH, TT dimer, keratinocyte viability, and tyrosinase tests. These tests were performed as follows.

a. Elastase and Collagenase Inhibition

Human dermal fibroblasts were cultured and used as a source of the elastase enzyme. This enzyme was partially purified from the fibroblasts by lysing the cells in an elastase buffer and retaining the soluble portion of the lysate. Portions of this fibroblast lysate were then be incubated with test materials and a synthetic elastase substrate, Suc-(Ala3)-p-Nitroaniline (STANA). Elastase acts upon this substrate to release p-nitroaniline, which can be detected with a spectrophotometer by measuring the absorbance at a wavelength of 405 nm. An inhibition of the elastase enzyme is noted by a decrease in the amount of released p-nitroaniline when compared to uninhibited enzyme.

Matrix Metalloproteinase-1 (MMP-1) is an extracellular protease with an approximate molecular weight of 52-56 kD in its latent form. Upon cleavage of the proenzyme, the 22-46 kD MMP-1 becomes an active enzyme and can degrade many substrates including collagen, gelatin, and entactin. In human skin, increased MMP-1 activity can be induced via some disease states, exposure to UV irradiation or as part of the natural aging process. This can result an imbalanced state where the degradation of collagen by MMP-1 exceeds its rate of replacement. Therefore, materials that inhibit MMP-1 activity can be beneficial. To screen inhibitors of MMP-1 active human recombinant MMP-1 is incubated in the presence of a thiopeptolide substrate, potential inhibitors and 5,5'-dithiobis(2-nitrobenzoic acid) (DTNB). When the thiopeptolide substrate is broken down by MMP-1 it releases a sulfhydryl group that can react with DTNB and forms 2-nitro-5-thiobenzoic acid, which can be detected spectrophotometrically at 412 nm. Thus, MMP-1 activity will be proportional to the absorbance at 412 nm, and in the presence of inhibitors this absorbance will be decreased.

b. DPPH Assay

This assay is based on the measurement of the scavenging effect of antioxidants on the stable radical 2,2-diphenyl-1-picrylhydrazyl (DPPH). The free radical DPPH has a strong absorbance at 517 nm, and this absorbance is reduced when DPPH reacts with antioxidant compounds and is converted to hydrazine. The DPPH assay is considered a valid and easy assay to evaluate scavenging activity of antioxidants, since the radical compound is stable and does not have to be generated as in other radical scavenging assays.

c. TT Dimer Assay

The testing system used for this assay was the MatTek EpiDerm, a skin model which consists of normal human-derived epidermal keratinocytes cultured to form a multi-layered, highly differentiated model of the human epidermis. For this study, the tissues were treated topically either overnight with the test materials prior to UVB exposure (Pretreat group to assess prevention) or treated overnight after a UVB exposure (Post Treat group to assess repair). Following the exposures and treatments, the DNA was extracted from the EpiDerm tissues and assayed for thymine dimer content using an ELISA based method.

d. Ultraviolet-B Radiation Exposure on Keratinocyte Viability

Human epidermal keratinocytes were treated with the test materials for 24 hours and then exposed to a dose of UVB light (approximately 50 mj/cm$^2$). Changes in cell viability were then determined 24 hours post UVB exposure via an MTT assay. The MTT assay is a colorimetric analysis of the metabolic activity of the cell, which is a reflection of cell viability. Viable cells can take up MTT, which is then reduced by mitochondria resulting in the formation of insoluble purple formazin crystals. These crystals are then extracted from the cells with isopropanol and quantified spectrophotometrically. The intensity of the purple color is directly proportional to the number of viable cells and inversely proportional to the toxicity of the test material.

e. Tyrosinase Inhibition

Purified tyrosinase enzyme was mixed in a sodium phosphate buffer containing L-DOPA (L-3,4-dihydroxyphenylalanine) and incubated with the test material. After 30 minutes of incubation, the amount of L-DOPA converted to DOPA chrome (reflecting tyrosinase activity) is assessed by via a colorimetric assay. Kojic acid is the positive control for tyrosinase inhibition.

f. Results

Figure 5:
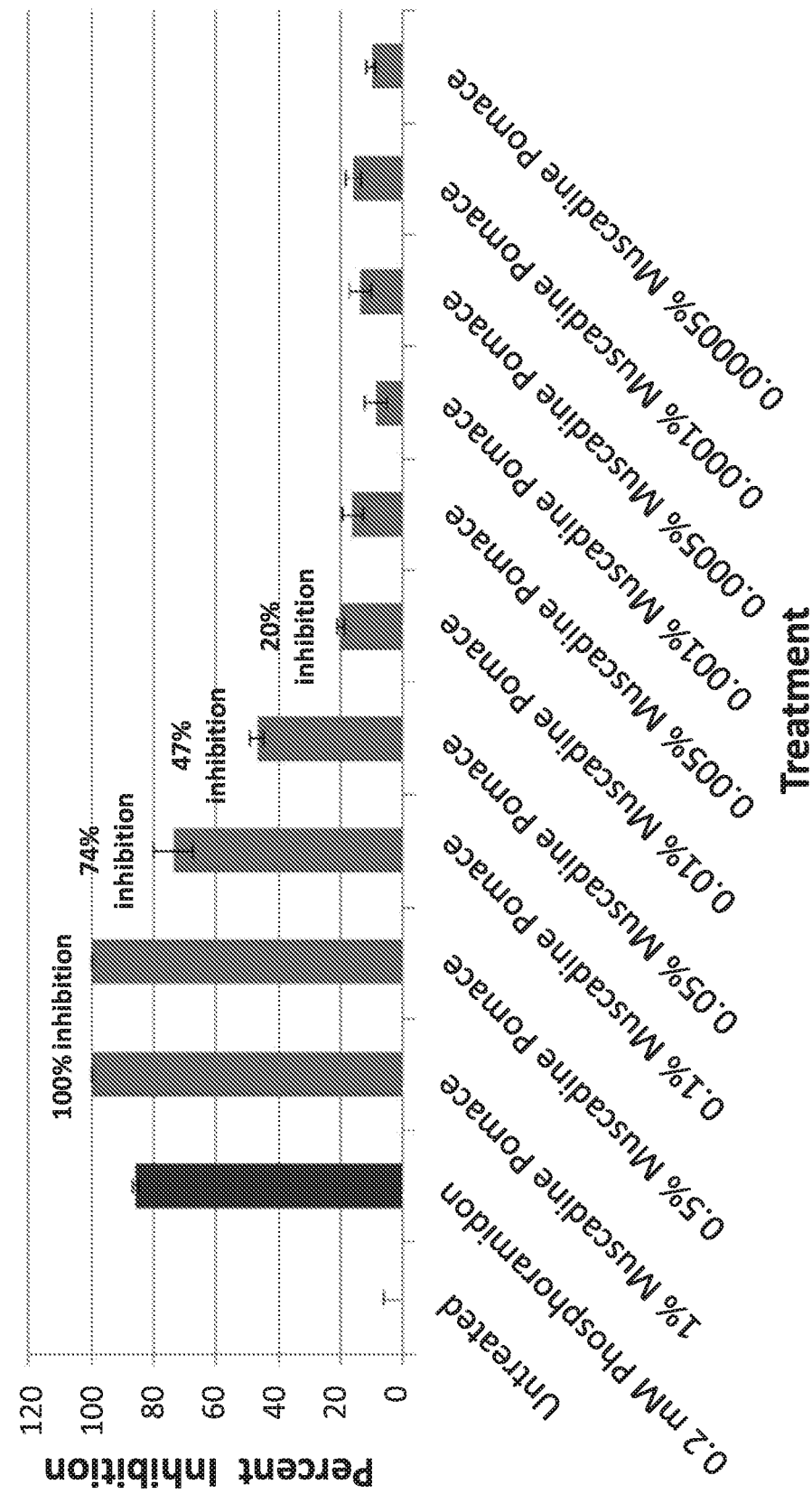
FIG. 5 is a graph illustrating the results of the elastase inhibition test with the decolorized muscadine pomace extract, demonstrating an effect on skin elasticity by inhibiting elastin reduction.
Figure 6:
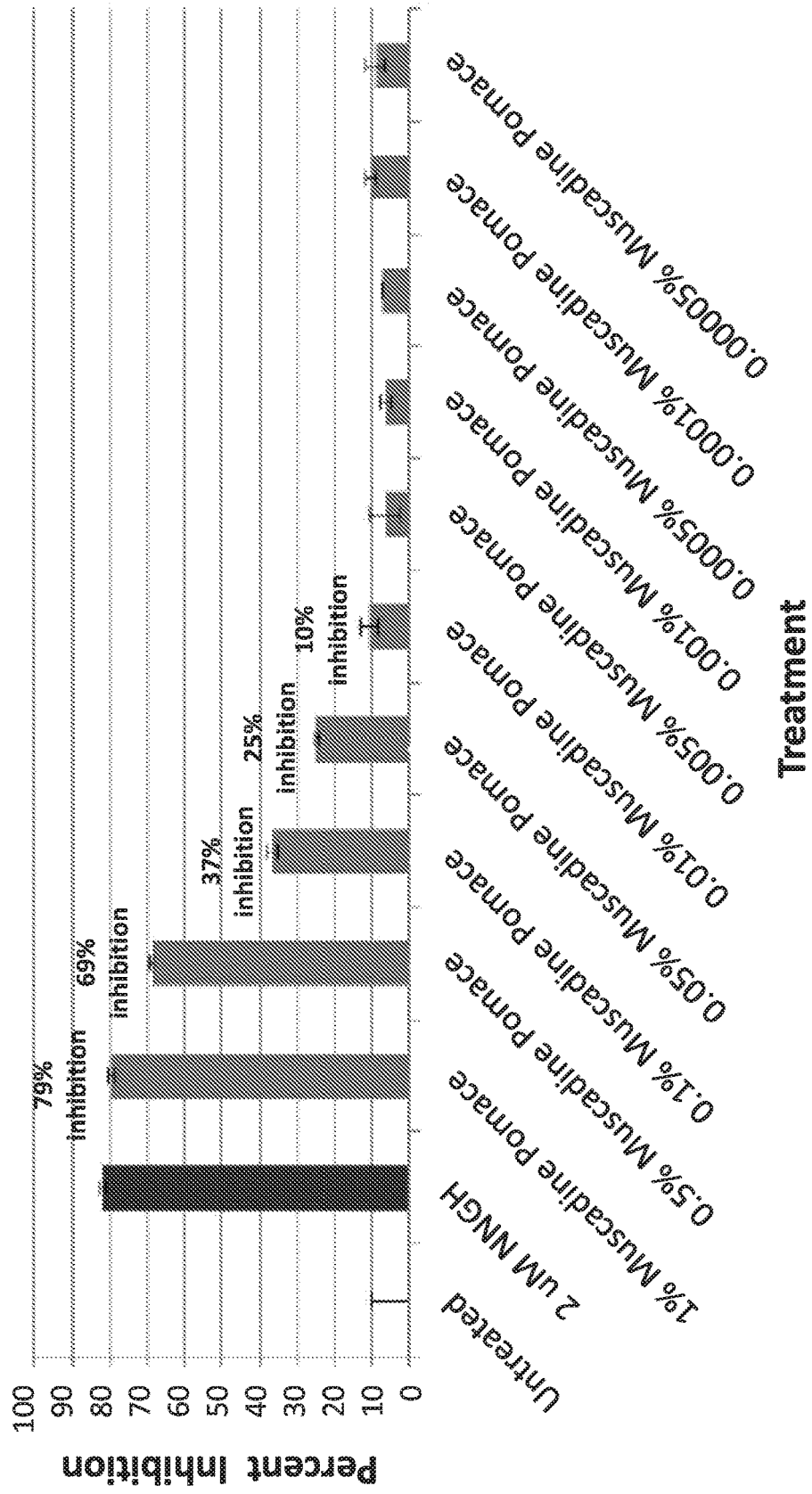
FIG. 6 is a graph illustrating the results of a collagenase inhibition test with the decolorized muscadine pomace extract. Enhanced collagenase inhibition improves skin firmness by avoiding collagen loss in the skin.
Figure 7:
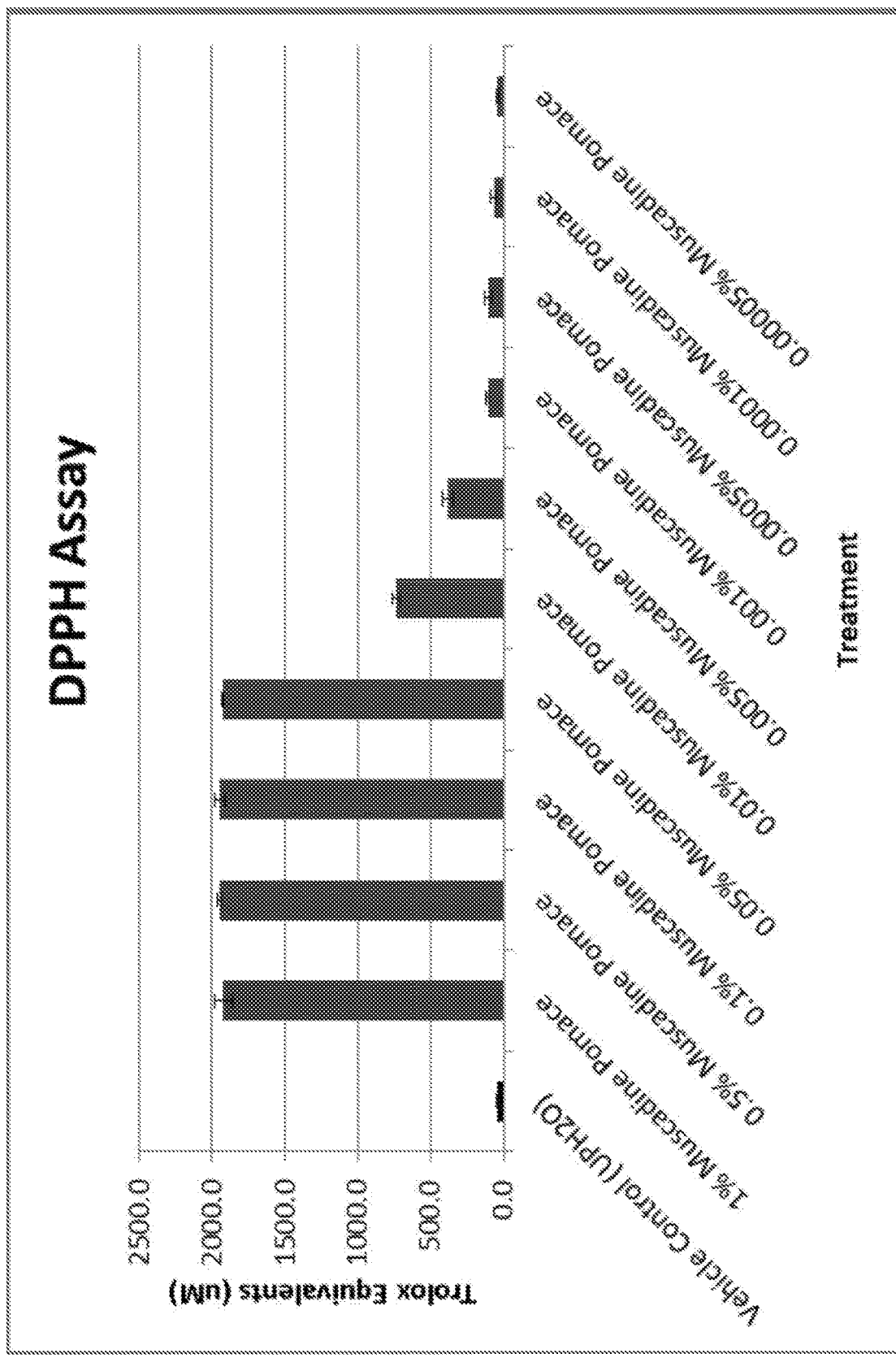
FIG. 7 is a graph showing the results of a DPPH assay (antioxidant power) that measures free radical scavenging power as shown in Trolox equivalents (TE). Decolorized muscadine pomace extract was used at several concentrations. Muscadine extract at 0.01% to 1% showed great free radical activity (TE) in the DPPH assay. Maximum activity was reached in this assay.
Figure 8:
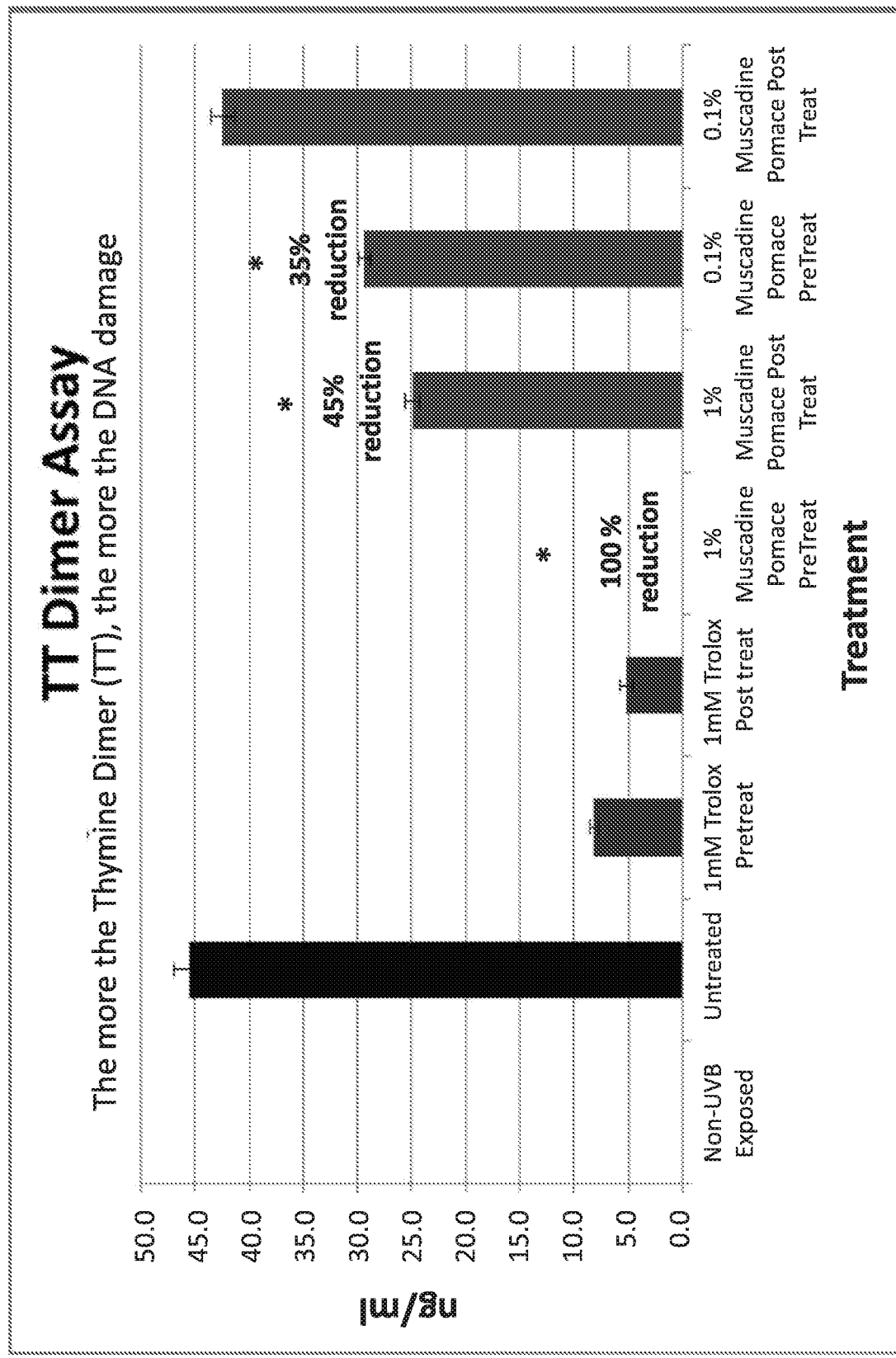
FIG. 8 shows the results of a TT Dimer Assay in which 1% decolorized muscadine pomace extract pretreatment before UVB exposure completely prevented DNA damage. The extract was better than the positive control (1 mM Trolox). A 1% decolorized muscadine extract treatment after UVB exposure (post-treatment) also showed 45% reduction in DNA damage, suggesting an effect on DNA repair; the effect from 0.1% was lower than 1% in both pre- and post-treatments.
Figure 9:
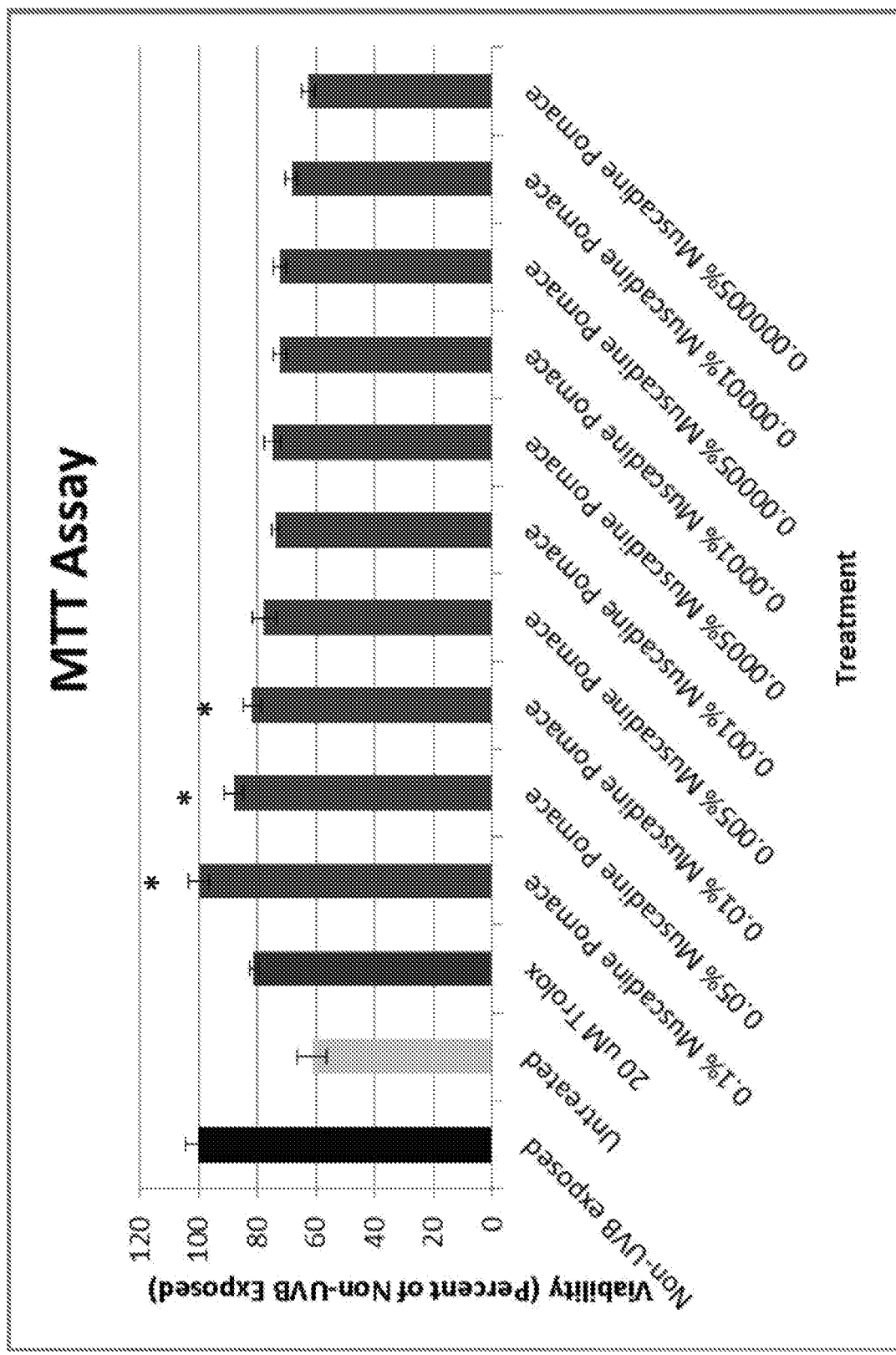
FIG. 9 shows cell survival after ultraviolet B exposure. The decolorized muscadine pomace extracts significantly increased cell survival as compared to untreated cells, and the increase was even better than for 20 μM Trolox (control).
Figure 10:
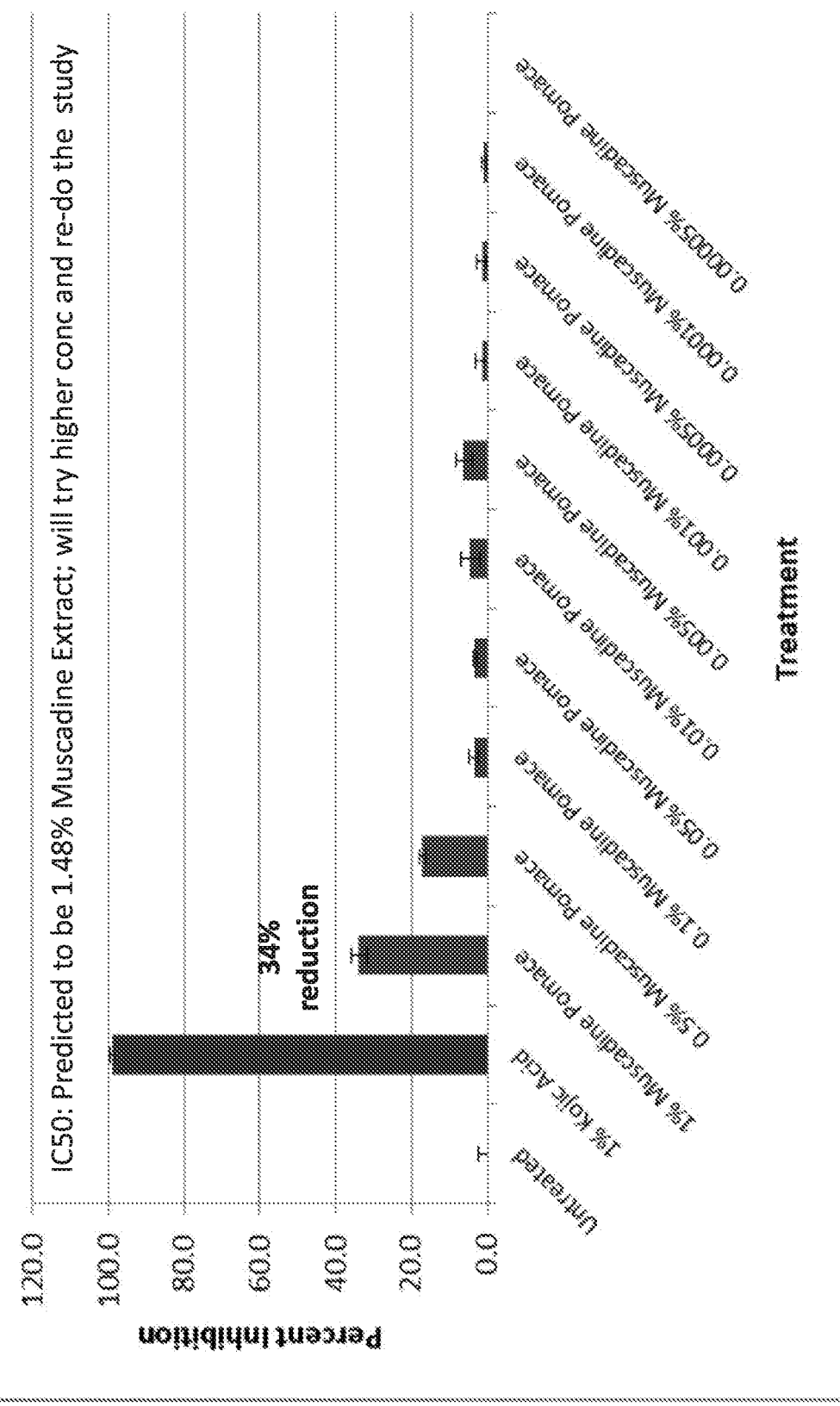
FIG. 10 shows tyrosinase inhibition at different concentrations of the decolorized muscadine pomace extract, indicating an ability to diminish hyperpigmentation.

FIG. 5 shows the results of the elastase inhibition test and demonstrates the potential effect on skin elasticity by inhibiting elastin reduction. FIG. 6 shows the results of a collagenase inhibition test that illustrates the potential to maintain skin firmness by avoiding collagen reduction. FIG. 7 shows the results of a DPPH assay that measures free radical scavenging power as shown in Trolox equivalents; the higher the TE value the greater the antioxidant power. The decolorized extract provided antioxidant activity greater than 1500 Trolox equivalents. FIG. 8 shows the results of a TT Dimer Assay in which 1% Muscadine extract pretreatment before UVB exposure completely prevented DNA damage. The extract was better than the positive control (1 mM Trolox); 1% muscadine extract treatment after UVB exposure (post-treatment) also showed 45% reduction in DNA damage, suggesting an effect on DNA repair; the effect from 0.1% was lower than 1% in both pre- and post-treatments. FIG. 9 shows cell survival after ultraviolet B exposure; the muscadine extracts significantly increased cell survival as compared to untreated cells, and the increase was even better than for 20 µM Trolox. FIG. 10 show tyrosinase inhibition, which suggests an ability to prevent hyperpigmentation. The decolorized extract was able to substantially inhibit tyrosinase, and would be expected to help avoid unwanted age- or exposure-related skin pigmentation.

Figure 11:
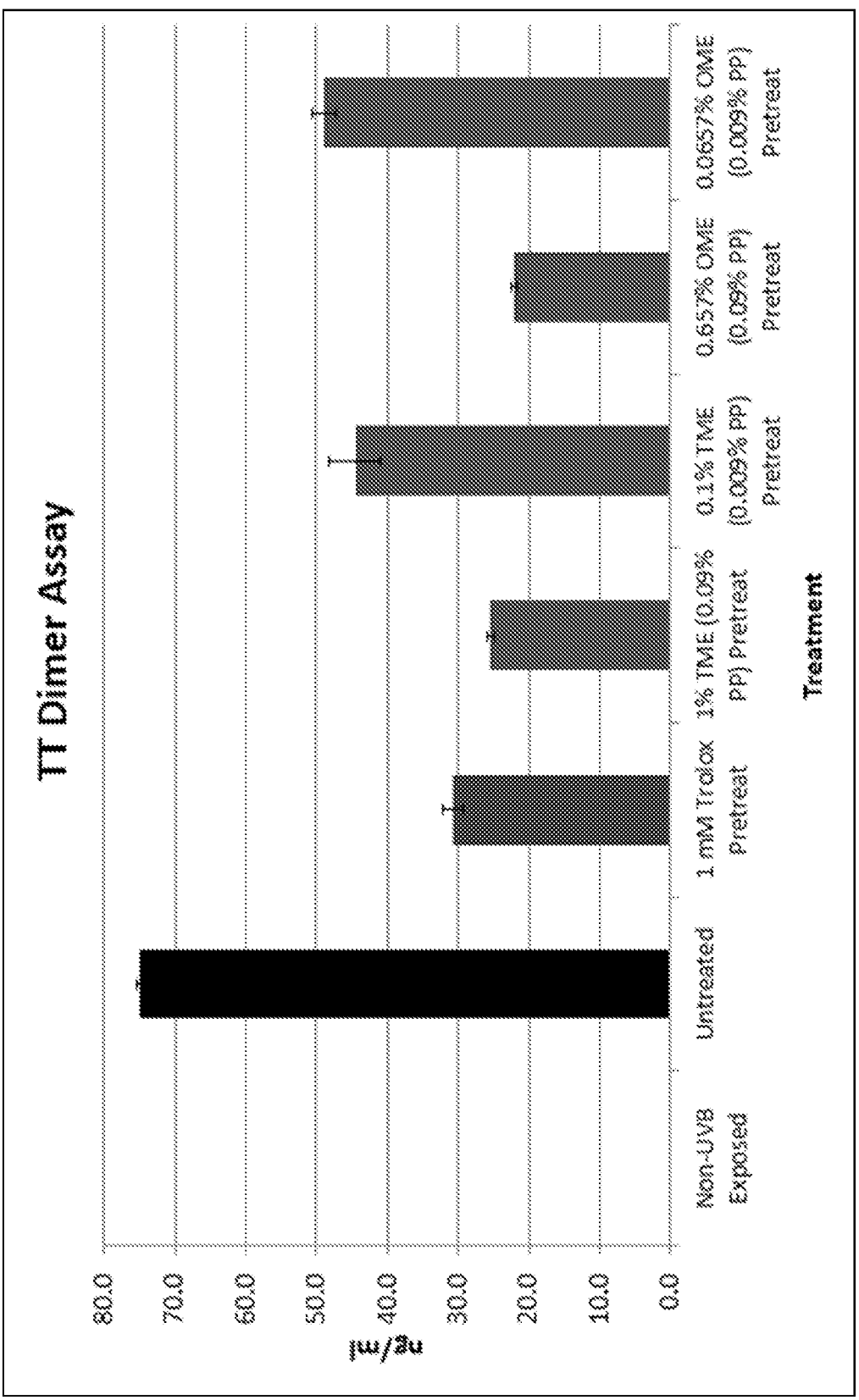
FIG. 11 is a graph of a TT Dimer DNA damage comparison assay between a decolorized topical muscadine pomace extract (TME) and orally administered muscadine pomace extract (OME) that has not been decolorized; there was no statistical difference in reducing DNA damage between OME and TME containing 0.09% and 0.009% of polyphenols. The OME is the extract disclosed in prior U.S. Pat. Nos. 8,568,804, 9,132,162 and 9,173,916.

FIG. 11 is a comparative assay that shows the decolorized extract retains the DNA protectant activity of the precursor extract. FIG. 11 is a graph of a TT Dimer DNA damage comparison assay between a decolorized topical muscadine pomace extract (TME) and orally administered muscadine pomace precursor extract (OME) that has not been decolorized. The OME is the extract disclosed in prior U.S. Pat. Nos. 8,568,804, 9,132,162 and 9,173,916. Both the TME and OME significantly prevented DNA damage caused by UV insult in the skin tissues as measured by reducing TT dimer formation when compared to the untreated group. There was no statistical difference between OME and TME for reducing DNA damage.

In summary, the disclosed muscadine extracts used at concentrations of 0.00001% to 1% by weight, such as, but not limited to 0.025% to 0.25% by weight in topical skin care products have lowered levels of condensed tannins and also demonstrate properties that are associated with improved skin elasticity and skin firmness, reduced dark spot formation, improved antioxidant activity by free radical scavenging, and protection from ultraviolet-B light, including enhanced skin repair and increased skin cell survival. Decolorization of the extract does not significantly affect the skin protective properties of the extract due to preservation of the overall phenolic profile of the decolorized extract.

2. Muscadine Pomace Extract Inhibits Protein Glycation

Advanced glycation end products (AGEs) are produced by attachment of sugar molecules to cellular and circulating proteins and lipids, a process accelerated by oxidative stress. A variety of AGE molecules have been detected within the body and importantly, increased levels of AGEs are associated with diseases such as diabetes, neurodegeneration, arthritis, and chronic inflammatory disorders. Moreover, a large body of evidence suggests that AGE accumulation underlies the normal process of aging—not only do AGE levels increase with chronological age, but interventions that prolong lifespan (such as caloric restriction) also reduce AGE levels. AGE levels increase in the skin during aging and it has been proposed that glycation of collagen and other skin proteins contributes to the altered appearance and function of aged skin.

Current research suggests that AGEs contribute to cellular aging and dysfunction through two mechanisms. First, the sugars can damage the proteins, interfering with normal function and decreasing cellular viability. Second, AGEs are thought to initiate a vicious cycle of inflammation through their interaction with the receptor for advanced glycation end products (RAGE); activation of RAGE induces multiple inflammatory pathways that ultimately lead to cellular death.

Some, but not all, polyphenols have been shown to inhibit the formation of AGE proteins. It was therefore determined if the decolorized topical muscadine extract (TME) containing reduced tannin levels retained the ability to inhibit protein glycation. Thus, the effects of TME were compared to those of the original/oral muscadine extract (OME). AGE formation was measured using a modification of the standard fluorescence assay as described in Farrar et al., BioFactors 30:193-200, 2007. Briefly, serum albumin is incubated with fructose in phosphate buffer for 72 hours at 37° C. and fluorescence intensity is measured at 370/440 excitation/emission wavelengths. Various concentrations of the muscadine extracts (standardized to µg polyphenols/ml buffer) were compared to control vehicle and results are expressed as percent inhibition of AGE formation produced in the control (vehicle) samples.

Figure 12:
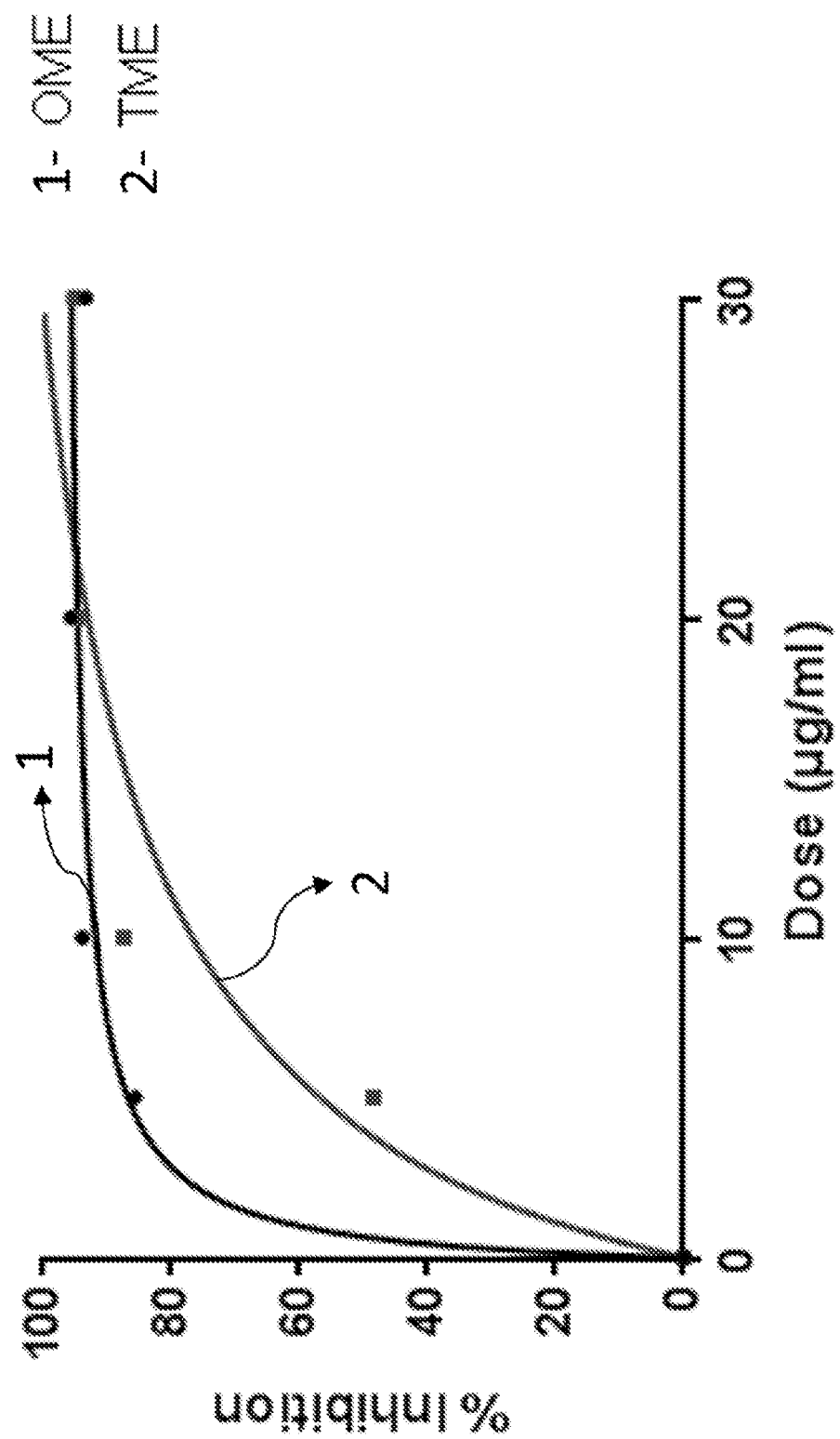
FIG. 12 is a graph illustrating that both the OME and TME demonstrated excellent activity (efficacy) in inhibiting Advanced Glycation Endproducts (AGE) formation in a dose-related manner. Maximal inhibition of AGE formation reached 95-100% at concentrations of 15-20 μg polyphenols/ml for both extracts. However, the OME was more potent than the TME as indicated by the concentrations required to inhibit AGE formation by 50% ($IC_{50}$). The $IC_{50}$ value for the OME was 0.65 μg polyphenols/ml whereas the $IC_{50}$ value for the TME was 3.94 μg polyphenols/ml. This suggests that while tannins contribute to the AGE-inhibitory activity, the other muscadine polyphenols remaining in the TME are equally efficacious in inhibiting protein glycation as those found in the OME.

As shown in FIG. 12, both the OME and TME demonstrated excellent activity (efficacy) in inhibiting AGE formation in a dose-related manner. Maximal inhibition of AGE formation reached 95-100% at concentrations of 15-20 µg polyphenols/ml for both extracts. However, the OME was more potent than the TME as indicated by the concentrations required to inhibit AGE formation by 50% ($IC_{50}$). The $IC_{50}$ value for the OME was 0.65 µg polyphenols/ml whereas the $IC_{50}$ value for the TME was 3.94 µg polyphenols/ml. This suggests that while tannins contribute to the AGE-inhibitory activity, the other muscadine polyphenols remaining in the TME are equally efficacious in inhibiting protein glycation as those found in the OME.

D. Topical Compositions for Reducing Inflammation

Disclosed herein are topical compositions that include an effective amount of decolorized muscadine (*Vitis rotundifolia*) pomace solvent extract, beta-glucan and grape seed extract, and their use. The topical compositions may additionally include other ingredients that are present in a sufficient amount to reduce inflammation when applied to the skin, such as panthenol, Vitamin C and/or superoxide dismutase. For example, the topical compositions may also include an effective amount of Vitamin A, Vitamin E, or Vitamins A and E. The reduction in inflammation may include a reduction in the production of IL-1 alpha, IL-6, prostaglandin E2, or any combination thereof, by skin cells.

Given the known effects of inflammation on the skin, including inflammation as a result of UV radiation, the inadequacy of many conventional skin products to interfere with the mechanisms of dermal and epidermal cell damage, and the reluctance of the public to regularly wear sufficient protection to block the damaging effects of UV light, there is a need for effective alternative products that provide protection from the harmful effects of inflammation, such as, but not limited to, inflammation caused by UV light. The topical compositions disclosed herein achieve these objectives by combining several ingredients in a consumer-acceptable form, which at the same time effectively lowers the production of multiple markers of skin inflammation.

The decolorized muscadine pomace solvent extracts described herein, having a reduced content of condensed tannins, can be incorporated into a variety of topical compositions. These topical compositions have a polyphenol profile that is beneficial to the skin, but the compositions are relatively decolorized because of their lower condensed tannin content. As used herein, a "low condensed tannin content" means a condensed tannin content of 10% or less by weight. The compositions include a decolorized muscadine pomace extract, beta glucan, and grape seed extract.

1. Decolorized Muscadine Pomace Solvent Extracts

The disclosed compositions and methods contain a decolorized muscadine pomace extract that has a lower level of condensed tannin content as compared to a muscadine pomace extract that has not been decolorized. The decolorized muscadine pomace precursor extract can be prepared as disclosed above in sections A and B. Any of the compositions disclosed herein may contain decolorized muscadine pomace extract formulated for administration to the skin.

The extraction methods disclosed herein for selectively lowering the levels of condensed tannins, surprisingly and advantageously preserve or improve the levels of other polyphenols that are beneficial to the skin, while avoiding the drawbacks posed by the presence of high levels of condensed tannins. Methods of making the combined extracts include combining a bronze muscadine pomace extract with a purple muscadine pomace extract to produce a muscadine pomace extract, wherein the ratio of bronze muscadine pomace extract to purple muscadine pomace extract ranges from 0.1 to 10 (weight to weight), such as 0.3 to 3 (weight to weight). In certain examples, the decolorized muscadine pomace solvent extract is prepared from such a combined precursor extract.

The combined precursor extract can be made by separate extraction of bronze and purple muscadine grapes with subsequent combination of the extracts, or by simultaneous extraction of bronze and purple muscadine grapes combined in desired ratios. In the disclosed examples, the decolorized muscadine pomace solvent extract is an aqueous extract of the precursor combined liquid muscadine pomace.

In some embodiments, the ratio of bronze to purple muscadine pomace extract in the precursor liquid extract ranges from 0.1 to 10, such as 0.3 to 3. For example, the ratio of bronze muscadine pomace extract to purple muscadine pomace extract is about 2.75 to about 1 (weight to weight), 2.5 to about 1 (weight to weight), about 2.25 to about 1 (weight to weight), about 2 to about 1 (weight to weight), about 1.5 to about 1 (weight to weight), or about 1 to about 1 (weight to weight). In other examples, the ratio is about 10 to about 1, about 7.5 to about 1, or about 5 to about 1. As used herein the term "about" is defined as ±0.5. In a particular example, the ratio of bronze muscadine pomace extract to purple muscadine pomace extract is about 2.25 to about 1 (weight to weight).

In certain embodiments, the combined precursor muscadine (*Vitis rotundifolia*) pomace liquid extract has a polyphenol content of at least about 2%. For example, the polyphenol content is at least about 3%, at least about 3.5%, at least about 4%, at least about 4.5%, at least about 5%, at least about 6%, at least about 7%, at least about 8%, at least about 10%, at least about 12%, or at least about 14%. In a particular example, the combined precursor muscadine (*Vitis rotundifolia*) pomace liquid extract has a polyphenol content of about 4%.

In some embodiments, the disclosed combined precursor liquid muscadine pomace extracts include 20% to 50% solids, such as at least 25%, at least 30%, at least 35%, at least 37%, at least 40%, at least 42%, at least 44%, at least 46% or at least 48%, in a liquid. In a particular example, the combined precursor extract includes about 40% solids in a liquid.

In certain embodiments, the decolorized muscadine pomace solvent extract is a combination of liquid extracts of bronze and purple muscadine pomace. In some embodiments of the decolorized muscadine pomace solvent extract, the ratio of bronze muscadine pomace extract to purple muscadine pomace extract ranges from about 0.1 to about 10 (weight to weight), such as from about 0.3 to about 3 (weight to weight).

In some examples, the phenolic content of the decolorized muscadine pomace solvent extract includes about 2-3% ellagic acid and about 30-31% gallic acid, for example: about 2-3% ellagic acid, about 3-4% ellagic acid glycosides, about 30-31% gallic acid, about 2-3% quercetin, about 10-11% gallotannins, about 7-8% ellagitannins, about 29-30% proanthocyanidins, about 4-5% anthocyanins, about 2-3% catechins, and about 6-7% phenolic acids.

The purple muscadine pomace extracts used for the topical compositions may be comprised of an extract of whole purple (*Vitis rotundifolia*) muscadine grapes, an extract of purple muscadine pomace from other than whole grapes, or both. In an embodiment, the decolorized muscadine (*Vitis rotundifolia*) pomace solvent extract is obtained after an initial pressing, and comprises skin, seeds, pulp and residual juice.

In certain embodiments, the decolorized muscadine pomace solvent extract can include between about 7% and about 10% polyphenols, such as about 9% to about 10% polyphenols, and less than about 5% monosaccharides, such as less than about 4% monosaccharides, by weight of the extract. In a particular example, the decolorized muscadine (*Vitis rotundifolia*) pomace solvent extract has a polyphenol content of about 9% to about 10%, and contains less than about 4% monosaccharides by weight of the decolored extract.

In some non-limiting examples, the condensed tannins are less than about 10% of the total polyphenol content of the decolorized muscadine pomace solvent extract. In additional non-limiting examples, the decolorized muscadine (*Vitis rotundifolia*) pomace solvent extract total polyphenols in the decolorized muscadine pomace solvent extract consist of at least about 85%, such as at least about 90%, polyphenols other than condensed tannins.

The decolorized muscadine (*Vitis rotundifolia*) pomace solvent extract may additionally include naturally occurring components from the grape pomace. For example, the decolorized muscadine pomace solvent extract may contain about 0.5%-5% fiber, about 7%-14% protein, about 0.5%-3% fat, and about 15%-20% organic acids by weight of the extract. In certain examples, the decolorized muscadine pomace solvent extract includes about 0.5%-2% or about 1%-2% fiber, about 7%-9% or about 7%-8% protein, about 0.05%-1% or about 0.1%-0.5% fat, and about 15%-17% or about 15.5-16.5% organic acids, with each percentage by weight of the extract.

2. Additional Components and Formulations

Beta-glucans are naturally occurring polysaccharides that contain beta-D-glucose, and are found in the cell walls of certain cereals, yeast, bacteria and fungi. In some examples, the beta-glucan is extracted from a cereal. In particular examples, the beta-glucan is extracted from oat, including the common oat *Avena sativa*. In certain examples, the beta-glucan has a molecular weight of between about 0.5-1.0×10$^6$ Da. The beta-glucan can be a polysaccharide of glucose, and may comprise both 1,4 and 1,3 beta glycosidic linkages.

Beta-glucan is believed to provide health benefits, including but not limited to, smoothing skin, moisturizing skin, stimulating fibroblast growth and/or collagen synthesis, reducing the discoloration of scars, and stimulating the immune defense.

Grape seed extract is derived from whole grape seeds and contains beneficial dietary components. Grape seeds are waste products of the winery and grape juice industries. These seeds contain fiber, lipid, protein, carbohydrates, and generally about 4-8% polyphenols (dry weight) depending on the variety. Commercial extracts of grape seeds, including *Vitis vinifera* grape seed extracts, are often standardized to provide between 70-95% polyphenolics on a dry weight percentage.

The grape seed extract included in the topical compositions disclosed herein may be a *Vitis vinifera* grape seed extract. In some examples, the grape seed extract has a total polyphenol content of less than 70%, and in some examples the polyphenol content is less than 50%. In particular examples, the grape seed extract contains 38-50% polyphenols, 9-12% fiber, 1-2% protein, 25-30% sugars and less than 1% lipid.

In embodiments, the topical compositions comprise about 0.001% to about 1.0% of decolorized muscadine pomace solvent extract, such as about 0.01% to about 0.5% of decolorized muscadine pomace solvent extract, or about 0.025% to about 0.25% of decolorized muscadine pomace solvent extract, with percentages being based upon the total weight of the topical composition. In certain examples, the topical compositions comprise about 0.0001% to about 1.0% beta-glucan, such as about 0.0005% to about 0.1% beta-glucan, or about 0.005% to about 0.05% beta-glucan, with percentages being based upon the total weight of the topical composition. In further examples, the topical compositions comprise about 0.00001% to about 0.1% grape seed extract, such as about 0.0001% to about 0.05% grape seed extract, or about 0.0002% to about 0.01% grape seed extract, with percentages being based upon the total weight of the topical composition.

Embodiments of the topical compositions can comprise about 0.001% to about 1.0% of decolorized muscadine pomace solvent extract, 0.0001% to about 1.0% beta-glucan, and about 0.00001% to about 0.1% grape seed extract, with percentages being based upon the weight of the topical composition. For example, the topical composition can comprise about 0.01% to about 0.5% of decolorized muscadine pomace solvent extract, about 0.0005% to about 0.1% beta-glucan, and about 0.0001% to about 0.05% grape seed extract, by weight of the topical composition. In further examples, the topical composition comprises about 0.025% to about 0.25% of decolorized muscadine pomace solvent extract, about 0.005% to about 0.05% beta-glucan, and about 0.0002% to about 0.01% grape seed extract, by weight of the topical composition.

The topical compositions disclosed herein can also include Vitamin A (retinol and its analogues, such as retinyl palmitate) and/or Vitamin E (tocopherol and its analogues, such as tocopheryl acetate). In certain examples, the topical compositions comprising a decolorized muscadine pomace solvent extract, beta-glucan and grape seed extract, also include an effective amount of Vitamin A, Vitamin E, or both Vitamins A and E. In certain disclosed embodiments, the topical compositions comprising a decolorized muscadine pomace solvent extract, beta-glucan and grape seed extract, further include panthenol, Vitamin C (and its analogues, such as magnesium ascorbyl phosphate, ascorbyl palmitate, etc.), and superoxide dismutase, which are present in a sufficient amount to reduce inflammation when applied to the skin.

The disclosed compositions can include additional ingredients. In some embodiments, the topical composition includes, by weight of the composition, about 0.0001% to about 0.5% Vitamin A, about 0.00001 to about 0.1% Vitamin C, about 0.001% to about 1.0% Vitamin E, about 0.001% to about 1.0% panthenol, about 0.00001% to about 0.1% superoxide dismutase, or any combination thereof. In non-limiting examples of topical compositions that contain Vitamins C, A and/or E, the Vitamin C may be in the form of magnesium ascorbyl phosphate; the Vitamin A may be in the form of Vitamin A palmitate; and the Vitamin E may be in the form of Vitamin E acetate.

In certain examples, the compositions that include panthenol, Vitamins C, A or E, superoxide dismutase, or any combination of panthenol, Vitamins C, A and E, and superoxide dismutase, can reduce the production of IL-1 alpha, IL-6, prostaglandin E2, or any combination of IL-1 alpha, IL-6, and prostaglandin E2, when topically applied to the skin.

Topical compositions comprising a decolorized muscadine pomace solvent extract, beta-glucan and grape seed extract, can also contain perfumes, preservatives, dyes, softeners, and physical reflectors, as well as any other class of materials whose presence may be cosmetically or otherwise desirable. Examples of skin care products that may include the topical compositions disclosed herein, include a gel oil cleanser, retinol serum concentrate, a day moisturizer, clarifying treatment toner pads, and facial skin renewal cream.

The topical compositions may be in the form of a liquid, gel or semi-solid. The selection of ingredient type and amount is dictated by the nature of the composition, i.e. gel or semi-solid, and is within the skill of cosmetic chemists. For example, larger amounts of wax are incorporated into the semi-solid compositions of the present invention than into the liquid ones.

Sunscreens alone may be unable to completely protect the skin against the adverse effects of ultraviolet radiation, thus alternative modes of protection have been proposed. Vitamins, such as Vitamin E acetate, have been shown to make the skin softer and smoother after topical application, which can offset some of the damaging effects of the sun. Vitamin A palmitate has been shown to create smoother skin and help enhance the process of cellular turnover. This enhancement rids the skin of the outermost dead layer of skin by bringing more youthful appearing skin cells to the surface.

Any skin care product made with the topical compositions described herein may additionally include a sunscreen. The disclosed topical compositions can be applied to skin before or after exposure to ultraviolet radiation. Daily application of the topical compositions may be used, even if exposure to the sun is not anticipated, to diminish the aging effects of inflammation in the skin.

E. Methods of Reducing Inflammation

The topical compositions can include beta-glucan, grape seed extract, or both beta-glucan and grape seed extract, in sufficient amounts to reduce inflammation when applied topically to skin. Inflammation can result from exposure to UV radiation, including ultraviolet B (UVB) radiation. Ultraviolet A (UVA) radiation is from light with a wavelength between 315 and 400 nm, and UVB radiation is from light with a wavelength between 280 and 315 nm.

UV radiation can be beneficial, in that it causes the body to produce vitamin D and can treat certain skin conditions. Overexposure to UV radiation, however, can cause significant skin damage including sunburn (erythema) and blistering (edema). Exposure to ultraviolet light can also cause the skin to feel dry and taut in moderate doses, and to peel if exposed to higher doses. These acute, or short term, effects are readily perceptible. However, there are also more subtle acute effects that are not as readily discernable, such as photo-immunosuppression, cross-linking of deoxyribonucleic acid (DNA), formation of sunburn cells, and loss of Langerhans cells. Even more serious long term effects can occur, such as skin cancer and premature aging of the skin.

Compositions which reduce inflammation may be identified by a reduction in the production of inflammatory mediators, including cytokines and prostaglandins. In some examples, the reduction of inflammation comprises a reduction in the production of an inflammatory mediator in a cell treated with a topical composition as described herein, as compared to the amount of the inflammatory mediator produced in a control cell. For example, the inflammatory mediator which is reduced can be IL-1 alpha, IL-6, or prostaglandin E2, or any combination of IL-1 alpha, IL-6, and prostaglandin E2. In certain examples, the control cell is a cell that is untreated with the topical composition. Alternatively, the control cell is a cell that is treated only with a carrier, excipient, or another composition comprising inactive ingredients.

In some examples, methods of reducing inflammation in a subject by applying a topical composition including an effective amount of decolorized muscadine pomace solvent extract, beta-glucan, and grape seed extract, are presented, including inflammation that is a result of exposure to UV radiation. Reducing inflammation, including inflammation that is caused by exposure to UV radiation, can ameliorate and/or prevent both damaging short term and long term effects to the skin. It was surprisingly found that a topical composition comprising a combination of decolorized muscadine pomace solvent extract, beta-glucan and grape seed extract can reduce inflammation in dermal cells, as measured by the assays of Examples 2-4.

The disclosed decolorized muscadine pomace solvent extracts, which have lower levels of condensed tannins compared to standard muscadine pomace extracts, surprisingly and advantageously preserve or improve the levels of other polyphenols that are beneficial in treatment of the skin while avoiding the drawbacks posed by the presence of high levels of condensed tannins. Topical compositions that include effective amounts of the decolorized muscadine pomace solvent extracts described herein, beta-glucan, and/or grape seed extract, are able to reduce inflammation when applied topically to skin, as demonstrated by bioassays as described in the Examples. Exemplary results and presented in FIGS. 13-15. These bioassays have demonstrated the mode of action of the reduction of skin inflammation by the topical compositions, as evidenced by lowering the production of inflammatory mediators in a human skin model (MatTek EpiDerm).

In view of these results, the topical compositions disclosed herein, comprising decolorized muscadine pomace solvent extract, beta-glucan, and grape seed extract, may be useful in methods of reducing inflammation in a subject by applying an effective amount of a disclosed topical composition to the skin. The subject can be healthy or an unhealthy subject. The subject can be a female or a male subject. The skin inflammation may be a result of exposure to ultraviolet radiation, including UVB radiation.

The topical compositions disclosed herein, comprising decolorized muscadine pomace solvent extract, beta-glucan, and grape seed extract, may also be useful for methods of inhibiting the production of an inflammatory mediator in a skin cell of a subject by applying an effective amount of a topical composition to the skin, to reduce the production of the inflammatory mediator. In some examples, the application of a topical composition inhibits the production of a subset of cytokines, such as IL-1 alpha and IL-6, and also the production of a subset of prostaglandins, such as prostaglandin E2. In an embodiment, the inflammatory mediator is IL-1 alpha, IL-6 or prostaglandin E2. In certain embodiments, the inflammatory mediator is any combination of IL-1 alpha, IL-6 and prostaglandin E2.

In further examples, disclosed are methods of inhibiting skin damage induced by UV radiation in the skin of a subject. These methods include topical application to the skin of an effective amount of a topical composition comprising an effective amount of decolorized muscadine pomace solvent extract, beta-glucan, and grape seed extract. The application of this topical composition after exposure to the UV radiation inhibits damage to the skin. The method can result in a reduction of the production of an inflammatory mediator. In certain examples, the inflammatory mediator is IL-1 alpha, IL-6 or prostaglandin E2. In an example, the inflammatory mediator is any combination of IL-1 alpha, IL-6 and prostaglandin E2.

Any of the aforementioned methods may be used to treat a healthy subject, meaning that the subject does not have any pathogenic skin conditions and only exhibits non-pathogenic skin inflammation prior to treatment. In certain examples, the methods are used to treat a female subject or a male subject.

III. Examples

Example 1

The MatTek EpiDerm model utilizes normal human-derived epidermal keratinocytes that have been cultured to form a multilayered, highly differentiated model of the human epidermis. Ultrastructural analysis has revealed the presence of keratohyalin granules, tonofilament bundles, desmosomes, and a multi-layered stratum corneum containing intercellular lamellar lipid layers arranged in patterns characteristic of in vivo epidermis. Markers of mature epidermis specific differentiation such as pro-filaggrin, the K1/K10 cytokeratin pair, involucrin, and type I epidermal transglutaminase have been localized in this model. The MatTek EpiDerm is also mitotically and metabolically active.

The cytokines IL-1 alpha and IL-6 are synthesized and stored in keratinocytes, and have been identified as mediators of skin irritation and inflammation. Release of these cytokines can be directly measured in tissue culture media via a colorimetric based enzyme linked immunosorbent assay (ELISA). Briefly, antibodies covalently linked to a solid support will bind any IL-1 alpha or IL-6 present in spent culture media samples. A second antibody that is covalently attached to an acetylcholinesterase enzyme will in turn detect any bound IL-1 alpha and IL-6. Upon addition of an appropriate color substrate, the acetylcholinesterase enzyme will generate a colored end product that can be measured spectrophotometrically.

Similarly, prostaglandin E2 release can be directly measured in tissue culture media via a colorimetric based competitive ELISA. For this assay, PGE2 molecules bound to an alkaline phosphatase enzyme compete with unlabeled PGE2 present in the tissue culture media for binding to anti-PGE2 antibodies in solution. The anti-PGE2 antibodies then bind to secondary antibodies linked to a solid support. A substrate solution is added which allows the alkaline phosphatase enzyme linked PGE2 to generate a colored end product that can be measured spectrophotometrically. In this assay, as the amount of PGE2 in the sample increases as the amount of recovered alkaline phosphatase linked PGE2 decreases. Therefore, the amount of PGE2 in the sample is inversely proportional to the amount of colored end product formed.

The bioactivity of certain embodiments of the disclosed topical compositions were compared to an over the counter topical hydrocortisone preparation as a positive control, as well as to UVB-exposed tissue not treated with any topical composition ("Untreated") and to non-UVB exposed tissue not treated with any topical composition ("Non-UVB Exposed"), as negative controls. Two percent DMSO was used as a blank control for the mixture of ingredients, since DMSO is used to help dissolve the ingredients, and DMSO is known to influence the inflammatory response. All assays were done in triplicate.

In the bioassays, the tissues that were not treated with either UV radiation or a topical composition are labelled "Non-UVB Exposed." Tissues treated with an over the counter composition containing 1% hydrocortisone are labeled "1% Hydrocortisone." Tissues that were untreated with a topical composition but were exposed to UVB radiation are labeled "Untreated." Tissues treated with a solution of 2% DMSO are labeled "2% DMSO." The TME extract labeled as "TME 1" in Table 5, which was used for the "Min TME" composition, contained 0.025% of decolorized muscadine pomace solvent extract. The TME extract labeled as "TME 2" in Table 5, which was used for the "Max TME" composition, contained 0.25% of decolorized muscadine pomace solvent extract. The compositions labeled as "Min Blend" and "Max Blend" contained the amounts of ingredients listed in Table 5; the composition labeled as "Min Blend+TME 1" contained both the Min Blend ingredients and the TME 1 ingredient, and the composition labeled as "Max Blend+TME 2" contained both the Max Blend ingredients and the TME 2 ingredient.

The Blends and TME/Blend mixtures contained the ingredients as listed in Table 5 (below), with the listed percentages based upon the total weight of the final composition:

TABLE 5

Ingredients used in the Topical Compositions of Examples 2-4 (w/w).

| ingredient | Min Blend | Max Blend | Min Blend + TME 1 | Max Blend + TME 2 |
|---|---|---|---|---|
| beta-glucan with glycerin/water | 0.005% | 0.05% | 0.005% | 0.05% |
| grape Seed Extract with glycerin/water | 0.0002% | 0.01% | 0.0002% | 0.01% |
| vitamin A as retinyl palmitate with tocopherol | 0.0005% | 0.01% | 0.0005% | 0.01% |
| vitamin E as tocopheryl acetate | 0.01% | 0.1% | 0.01% | 0.1% |
| vitamin C as magnesium ascorbyl phosphate | 0.0001% | 0.001% | 0.0001% | 0.001% |
| vitamin B5 (as panthenol 50% with water) | 0.01% | 0.05% | 0.01% | 0.05% |
| superoxide dismutase | 0.0001% | 0.001% | 0.0001% | 0.001% |
| DMSO | 2% | 2% | 2% | 2% |
| decolorized muscadine pomace solvent extract (TME) | — | — | 0.025% "TME 1" | 0.25% "TME 2" |

Example 2. Interleukin 1 Alpha (IL-1 Alpha)

Figure 13:
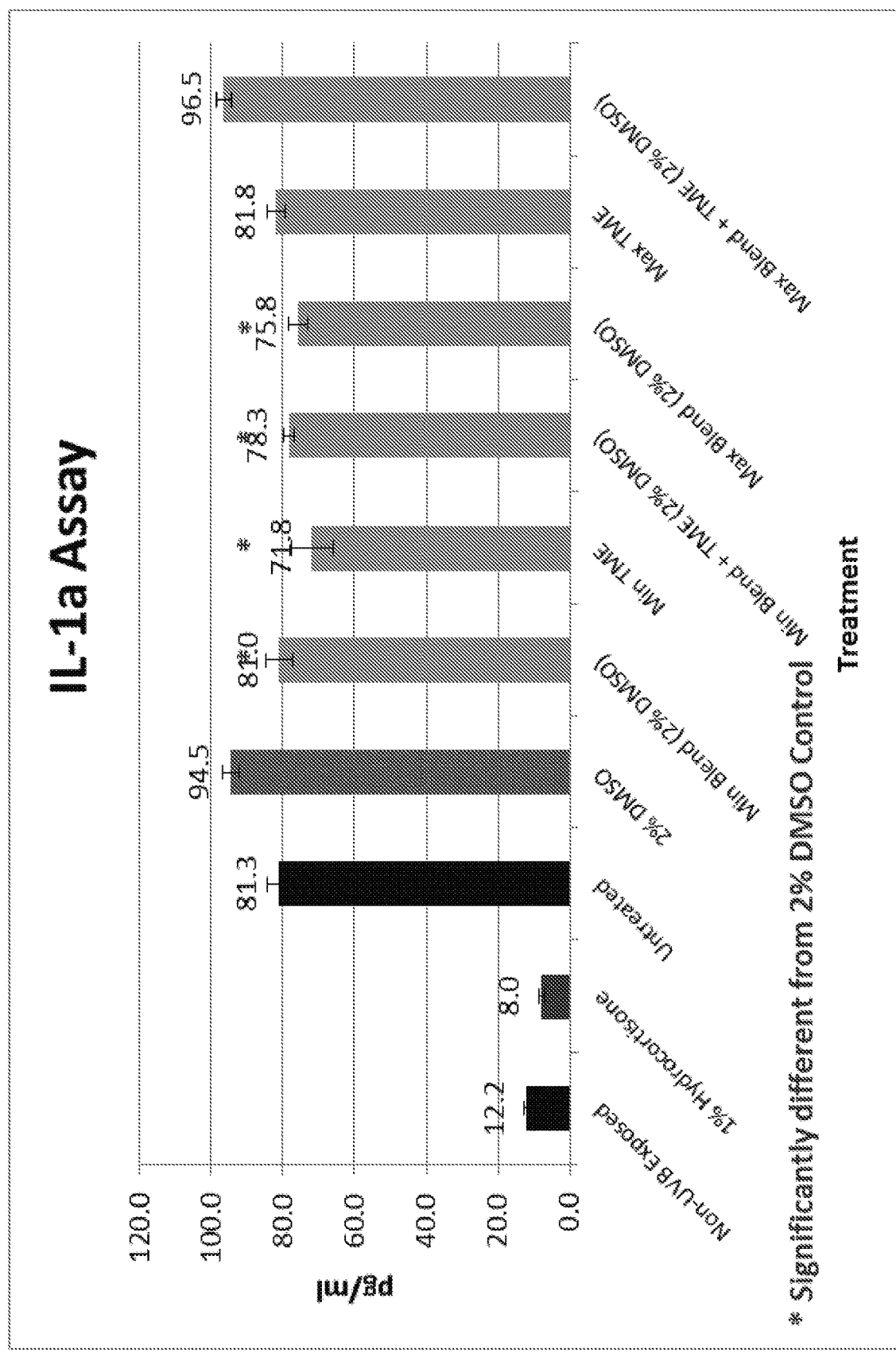
FIG. 13 is a graph illustrating the results of an inflammation test with a series of topical compositions, demonstrating an anti-inflammatory effect by inhibiting the production of interleukin 1 alpha (IL-1α or IL-1 alpha).

Exemplary topical compositions showed a reduction in the amount of IL-1 alpha produced in the epidermal keratinocytes of the MatTek EpiDerm model, as indicated in FIG. 13 and Table 6, below. The MatTek Full Thickness Tissues were allowed to incubate for at least 1 hour at 37±2° C. and 5±1% $CO_2$. After this initial incubation, the assay medium was replaced with 0.9 mL of fresh medium (37±2° C.). Three tissues were prepared for each test material.

An inflammatory response in the tissues was initiated via UV irradiation (UVB). A UV lamp was used to give a 300 $mJ/cm^2$ dose of UVB radiation to the tissues. Immediately after the application of the inflammatory stimuli, 50 μL (or 50 mg, for solid forms) of test material was applied directly onto the surface of the tissue.

An over the counter hydrocortisone cream was used as a positive control (treated post UVB only). For the "Untreated" negative control, tissues were exposed to the inflammatory stimuli but were not treated with any type of anti-inflammatory material. An additional set of tissues was left without exposure to the inflammatory stimuli ("Non-UVB Exposed") to provide a baseline measurement for the cytokines. The tissues were incubated at 37±2° C. and 5±1% $CO_2$ for 24 hours after exposure to the inflammatory stimuli. After the 24-hour incubation, the cell culture medium was collected and stored at −75° C. until it was analyzed for cytokines.

The IL-1 alpha ELISA plate was prepared by diluting the appropriate capture antibody in PBS. Next, 100 μL of the diluted capture antibody was added to the wells of a 96-well ELISA plate and the plate was incubated overnight at room temperature. On the following day, the plate was washed three times with 300 μL wash buffer (0.05% Tween 20 in PBS) and then blocked by adding 300 μL of blocking buffer (1% BSA in PBS) to each well. The plate was incubated with the blocking buffer for at least one hour. After the incubation, the blocking buffer was removed and the plate was washed three times as described above.

A series of IL-1 alpha standards was prepared and 100 μL of each of these standards was dispensed into two wells (duplicates) in the appropriate 96-well plate. Subsequently, 100 μL of each sample was added to additional wells and the plate was incubated for two hours at room temperature. After the incubation, the plate was washed three times as described above. Once the last wash was removed, 100 μL of a biotin conjugated detection antibody was added. After incubating the plate for two hours at room temperature, the plate was washed again as described above. 100 μL of HRP-streptavidin was then added to each well and the plate was incubated for 20 minutes at room temperature. Once the last wash was removed, 100 μL of substrate solution (hydrogen peroxide+tetramethylbenzidine as a chromagen) was added to each well. Once a sufficient level of color development had occurred, 50 μL of stop solution (2N sulfuric acid) was added to each well and the plate was read at 460 nm.

TABLE 6

IL-1 alpha data for exemplary topical compositions.

| treatment | IL-1 alpha (pg/mL) |
|---|---|
| Non-UVB Exposed | 12.2 ± 0.4* |
| 1% Hydrocortisone | 8.0 ± 0.8* |
| Untreated | 81.3 ± 3.2 |
| 2% DMSO | 94.5 ± 2.2 |
| Min Blend (with 2% DMSO) | 81.0 ± 3.7** |
| Min TME (TME 1) | 71.8 ± 5.9* |
| Min Blend + TME 1 (with 2% DMSO) | 78.3 ± 1.6** |
| Max Blend (with 2% DMSO) | 75.8 ± 2.6** |

TABLE 6-continued

IL-1 alpha data for exemplary topical compositions.

| treatment | IL-1 alpha (pg/mL) |
|---|---|
| Max TME (TME 2) | 81.8 ± 2.7 |
| Max Blend + TME 2 (with 2% DMSO) | 96.5 ± 2.1 |

*indicates values significantly different from the Untreated control ($p < 0.05$)
**indicates values significantly different from the 2% DMSO control ($p < 0.05$)

The data, shown graphically in FIG. 13, indicate that the Min Blend, the TME 1 composition (labeled as Min TME), the Min Blend+TME 1, and the Max Blend compositions inhibited the release the inflammatory mediator IL-1 alpha as compared to the 2% DMSO control in a statistically significant manner. In addition, the TME 1 composition (labeled as Min TME) also inhibited the release of the inflammatory mediator IL-1 alpha as compared to the untreated control ("Untreated") in a statistically significant manner.

Example 3. Prostaglandin E2 (PGE2)

Figure 14:
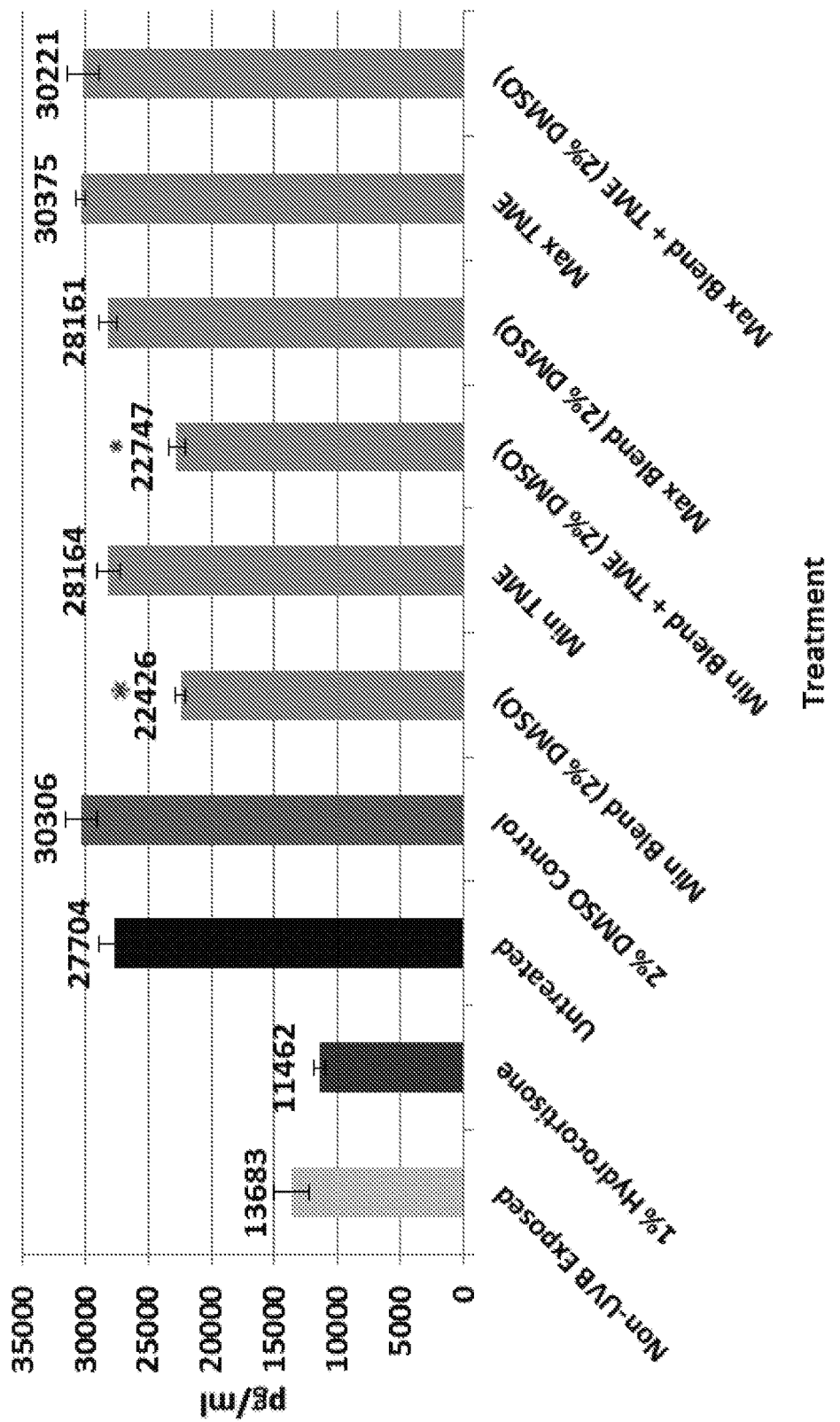
FIG. 14 is a graph illustrating the results of an inflammation test with a series of topical compositions, demonstrating an anti-inflammatory effect by inhibiting the production of prostaglandin E2 (PGE2).

Exemplary topical compositions showed a reduction in the amount of PGE2 produced in the epidermal keratinocytes of the MatTek EpiDerm model, as indicated in FIG. 14 and Table 7, below.

A series of PGE2 standards was prepared ranging from 7.8 pg/mL to 1000 pg/mL. An ELISA plate was prepared by removing any unneeded strips from the plate frame, remembering to designate two wells each for: total activity (TA) wells, non-specific binding (NSB) wells, maximum binding (MB) wells, and substrate blank wells (BO). 150 μL of tissue culture medium was added to the NSB wells while 100 μL of medium was added to the BO wells. 100 μL of standard or sample was then added to respective wells. To each of the wells used (except the TA and BO) 50 μL of the PGE2 Alkaline Phosphatase Conjugate was added. Next, 50 μL of PGE2 Alkaline Phosphatase Antibody solution was added to each well (except the TA, NSB and SD wells). The plates were covered and incubated at 2-8° C. for 18-24 hours. After the incubation, each well was washed three times with 400 μL of wash buffer. After the last wash, 5 μL of PGE2 Alkaline Phosphatase Conjugate was added to the TA wells and 200 μL of fresh Ellman's Reagent was added to each well. The plate was incubated at room temperature with periodic checks of the absorbance readings (405 nm) using a plate reader.

TABLE 7

PGE2 data for exemplary topical compositions.

| treatment | PGE2 (pg/mL) |
|---|---|
| Non-UVB Exposed | 13683 ± 1411* |
| 1% Hydrocortisone | 11462 ± 461* |
| Untreated | 27704 ± 1289 |
| 2% DMSO | 30306 ± 1277 |
| Min Blend (with 2% DMSO) | 22426 ± 392** |
| Min TME (TME 1) | 28164 ± 891 |
| Min Blend + TME 1 (with 2% DMSO) | 22747 ± 687** |
| Max Blend (with 2% DMSO) | 28161 ± 722 |
| Max TME (TME 2) | 30375 ± 392 |
| Max Blend + TME 2 (with 2% DMSO) | 30221 ± 1242 |

*indicates values significantly different from the Untreated control ($p < 0.05$)
**indicates values significantly different from the 2% DMSO control ($p < 0.05$)

The data, shown graphically in FIG. 14, indicate that the Min Blend and the Min Blend+TME 1 compositions inhibited the release the inflammatory mediator prostaglandin E2 as compared to the 2% DMSO control in a statistically significant manner.

Example 4. Interleukin 6 (IL-6)

Figure 15:
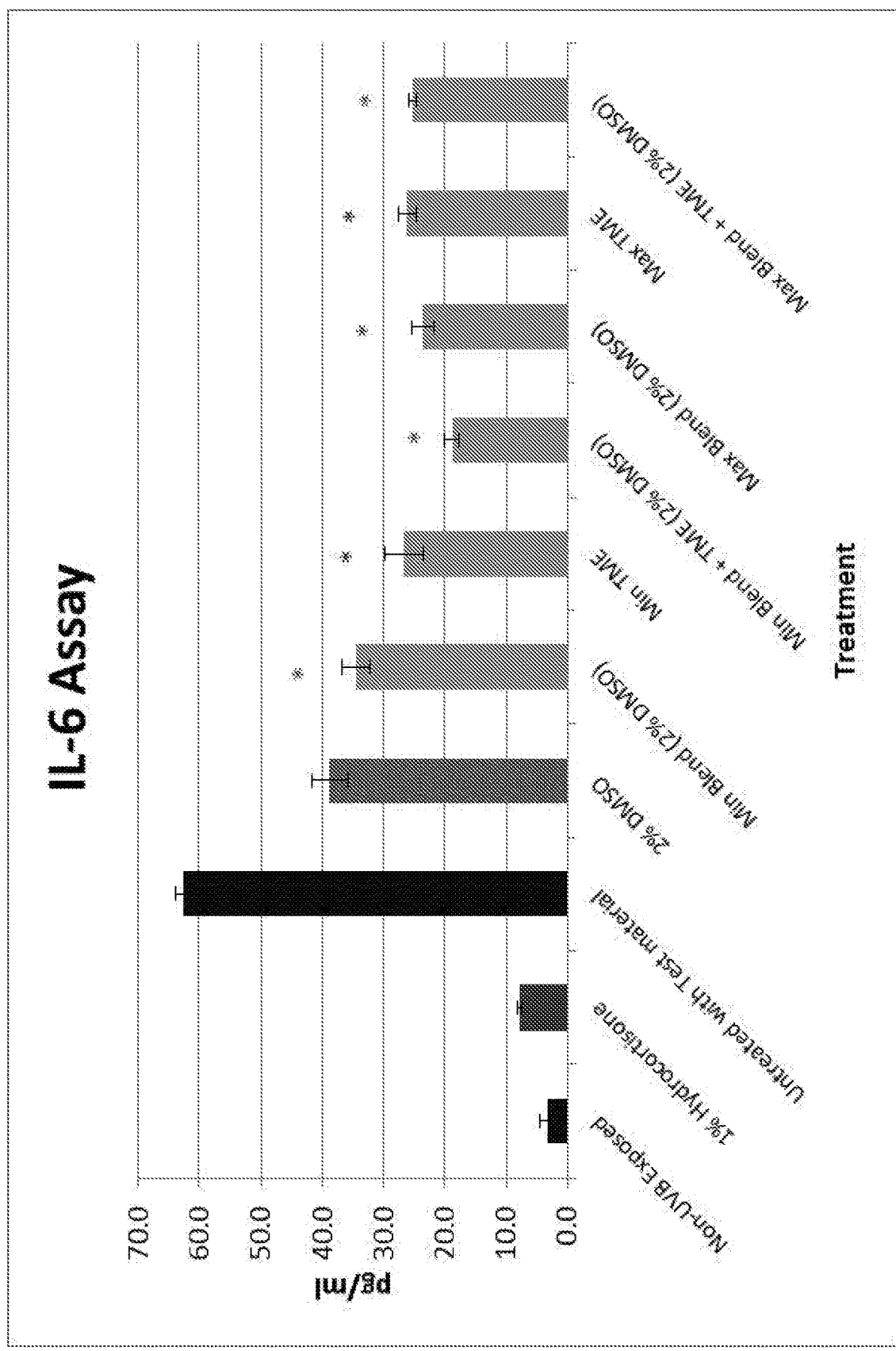
FIG. 15 is a graph illustrating the results of an inflammation test with a series of topical compositions, demonstrating an anti-inflammatory effect by inhibiting the production of interleukin 6 (IL-6).

Exemplary topical compositions showed a reduction in the amount of IL-6 produced in the epidermal keratinocytes of the MatTek EpiDerm model, as indicated in FIG. 15 and Table 8, below. The measurement of IL-6 was performed in the same manner as described in Example 2 for IL-1 alpha, substituting the IL-1 alpha-specific reagents with the corresponding IL-6-specific reagents.

TABLE 8

IL-6 data for exemplary topical compositions.

| treatment | IL-6 (pg/mL) |
| --- | --- |
| Non-UVB Exposed | 3.2 ± 1.3* |
| 1% Hydrocortisone | 7.9 ± 0.4* |
| Untreated | 62.8 ± 1.3 |
| 2% DMSO | 38.8 ± 2.9* |
| Min Blend (with 2% DMSO) | 34.5 ± 2.4 |
| Min TME (TME 1) | 26.6 ± 3.1* |
| Min Blend ± TME 1 (with 2% DMSO) | 18.8 ± 1.2** |
| Max Blend (with 2% DMSO) | 23.6 ± 1.8** |
| Max TME (TME 2) | 26.2 ± 1.5* |
| Max Blend ± TME 2 (with 2% DMSO) | 25.2 ± 0.6** |

*indicates values significantly different from the Untreated control ($p < 0.05$)
**indicates values significantly different from the 2% DMSO control ($p < 0.05$)

The data, shown graphically in FIG. 15, indicate that the Min Blend+TME 1, the Max Blend, and the Max Blend+TME 2 compositions inhibited the release the inflammatory mediator IL-6 as compared to the 2% DMSO control in a statistically significant manner. In addition, the TME 1 and TME 2 compositions inhibited the release of the inflammatory mediator IL-6 as compared to the Untreated control in a statistically significant manner.

In summary, the disclosed topical compositions comprising decolorized muscadine pomace solvent extracts, beta-glucan, and grape seed extract, are able to significantly reduce certain markers of inflammation, when used at concentrations of about 0.001% to about 1.0% by weight, about 0.0001% to about 1.0% by weight, and about 0.00001% to about 0.01% by weight, respectively. These topical compositions have low levels of condensed tannins yet the skin protective properties of the decolorized extract are retained due to preservation of its overall phenolic profile.

Thus, topical compositions comprising decolorized muscadine pomace solvent extracts, beta-glucan, and grape seed extract can reduce inflammation, including inflammation as a result of exposure to ultraviolet radiation, with a reduction in inflammation as measured by the assays of Example 2 (reduced IL-1 alpha production by epidermal cells), Example 3 (reduced prostaglandin E2 production by epidermal cells), and Example 4 (reduced IL-6 production by epidermal cells).

Figure 16:
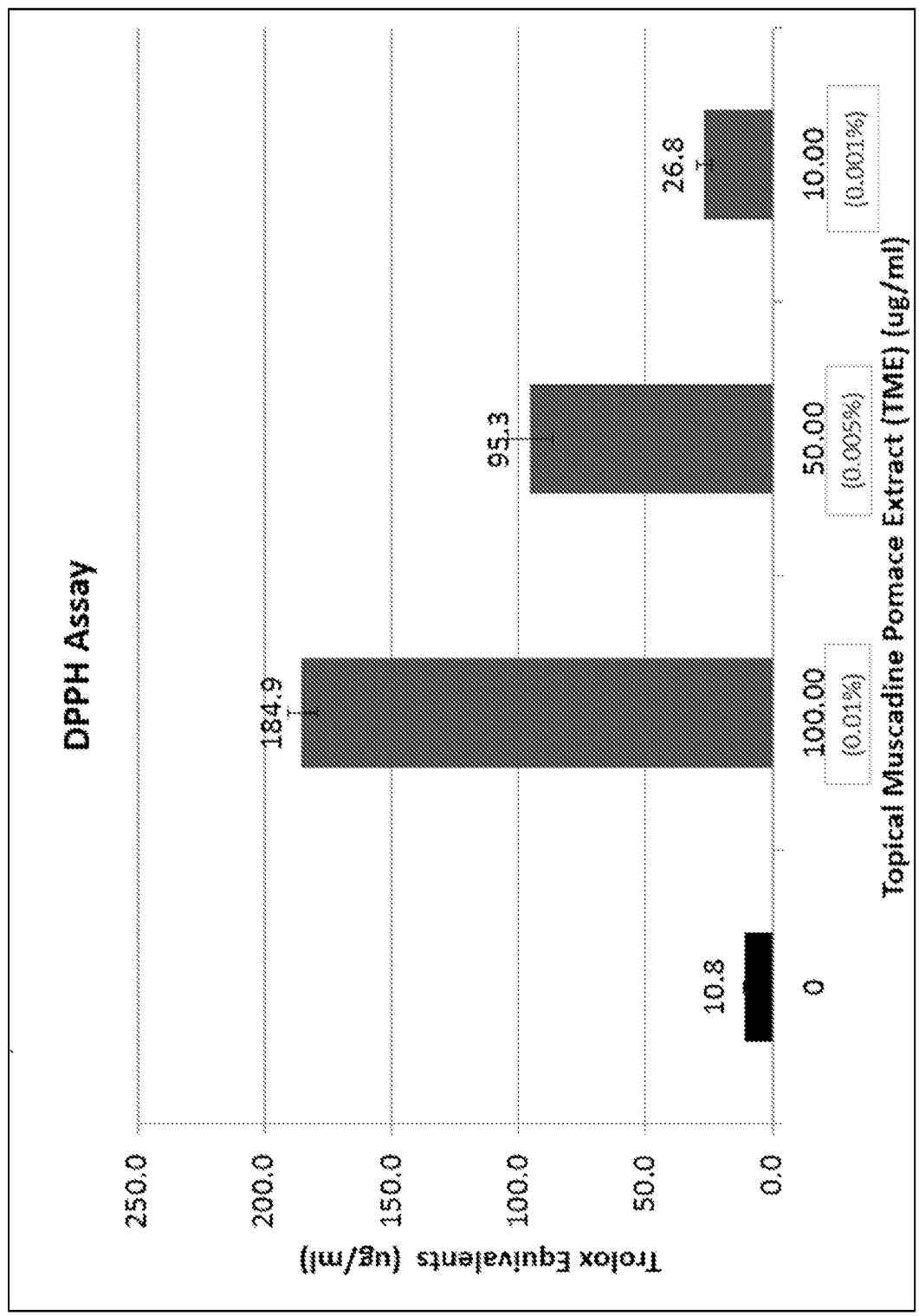
FIG. 16 is a graph illustrating the results of a DPPH assay with compositions of 0.01%, 0.005%, and 0.001% decolorized muscadine pomace extract (TME), by weight of the composition. See also FIG. 7. 1 gram of TME has the same antioxidant power as 1.85 grams of Trolox, suggesting TME is 185% more potent than Trolox as measured by DPPH assay.
Figure 17:
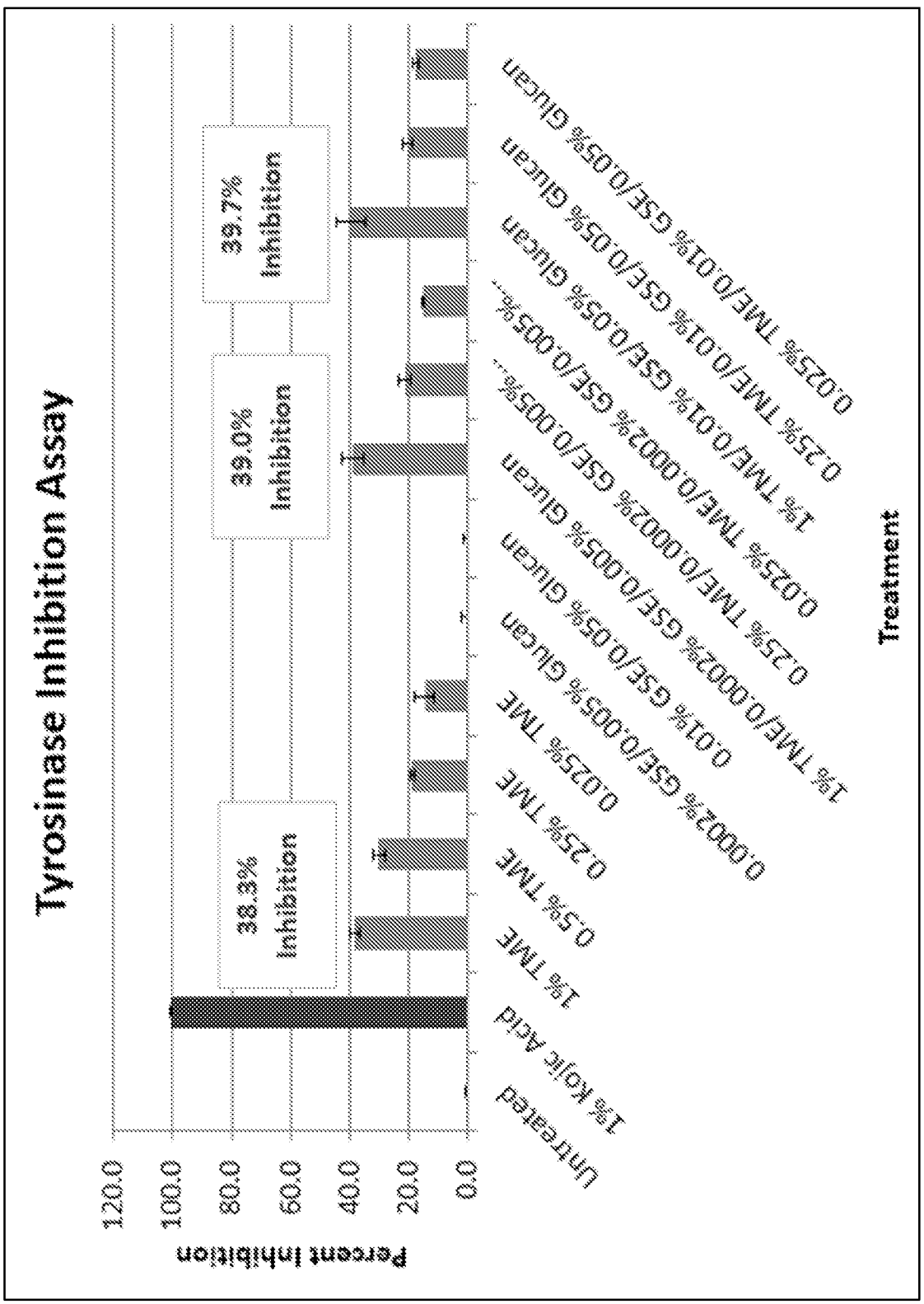
FIG. 17 is a graph illustrating tyrosinase inhibition with a series of additional topical compositions including a decolorized muscadine pomace extract.
Figure 18:
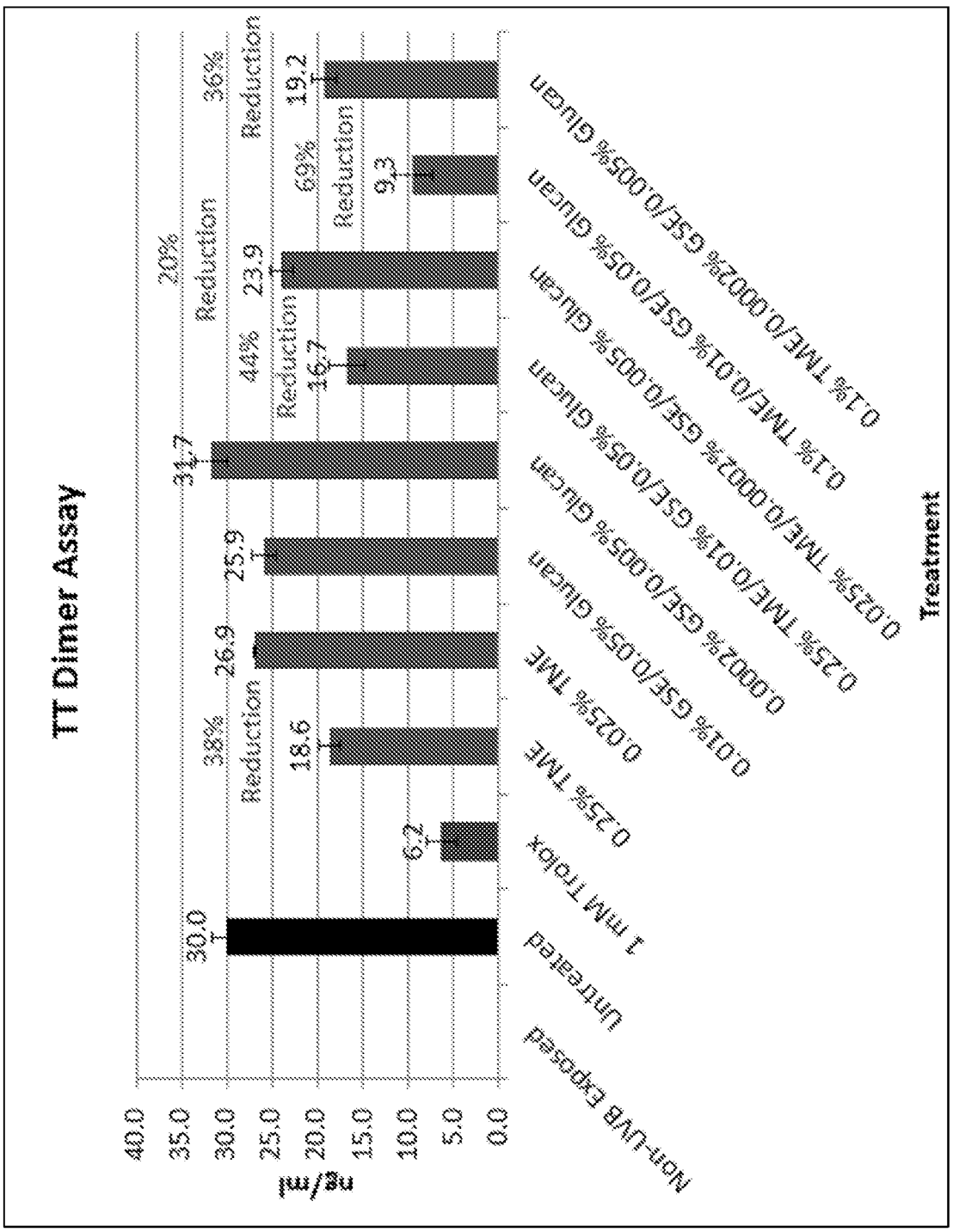
FIG. 18 is a graph illustrating TT (thymidine-thymidine) Dimer DNA damage with a series of additional topical compositions including a decolorized muscadine pomace extract.

Example 5. Activity of Additional Compositions Containing Decolorized Muscadine Pomace Extract Compositions comprising decolorized muscadine pomace solvent extracts exhibit antioxidant activity, as shown by testing such compositions in three assays: a DPPH assay, a tyrosinase inhibition assay, and a TT dimer assay. As shown in FIGS. 16-18, results of this testing indicate that grape extracts that undergo the decolorization processes disclosed herein retain their beneficial biological activity, including but not limited to their antioxidant activity, but do not contain the high levels of tannins that can stain the skin to which they are applied.

DPPH Assay. This assay is based on the measurement of the scavenging effect of antioxidants on the stable radical 2,2-diphenyl-1-picrylhydrazyl (DPPH). The free radical DPPH has a strong absorbance at 517 nm, and this absorbance is reduced when DPPH reacts with antioxidant compounds and is converted to hydrazine. The DPPH assay evaluates scavenging activity of antioxidants, since the radical compound is stable and does not have to be generated as in other radical scavenging assays.

FIG. 16 shows the results of a DPPH assay that measures free radical scavenging power as shown in Trolox equivalents; the higher the TE value, the greater the antioxidant power. Compositions of 0.01%, 0.005%, and 0.001% decolorized muscadine pomace extract (TME), by weight of the composition, showed dose-dependent antioxidant activity ranging from about 27 (at a concentration of 10 ug/ml) to about 185 (at a concentration of 100 ug/ml) Trolox equivalents.

Tyrosinase inhibition. Purified tyrosinase enzyme was mixed in a sodium phosphate buffer containing L-DOPA (L-3,4-dihydroxyphenylalanine) and incubated with the test material. After 30 minutes of incubation, the amount of L-DOPA converted to DOPA chrome (reflecting tyrosinase activity) is assessed by via a colorimetric assay. Kojic acid was used as the positive control for tyrosinase inhibition.

FIG. 17 shows the percent inhibition of tyrosinase activity in a series of compositions, including compositions containing varying amounts of decolorized muscadine pomace solvent extract, as compared to a positive control composition (1% kojic acid). The amount of decolorized muscadine pomace solvent extract ("TME" in FIG. 17) is shown as a weight percentage of the total composition. As indicated in FIG. 17, a composition containing 1% by weight of TME shows a 38.3% inhibition of tyrosinase activity.

TT Dimer Assay. The testing system used for this assay was the MatTek EpiDerm, a skin model which consists of normal human-derived epidermal keratinocytes cultured to form a multilayered, highly differentiated model of the human epidermis. For this study, the tissues were treated topically overnight with the test materials prior to UVB exposure. Following the exposures and treatments, the DNA was extracted from the EpiDerm tissues and assayed for thymine dimer content using an ELISA based method.

FIG. 18 shows the results of a TT Dimer Assay activity in cells treated with a series of compositions, including compositions containing varying amounts of decolorized muscadine pomace solvent extract, as compared to cells that were non-UVB exposed, untreated and treated with a composition containing 1 mM Trolox. Cells treated with compositions containing 0.25% (by weight of the total composition) decolorized muscadine pomace solvent extract pretreatment before UVB exposure showed statistically significant reductions in DNA damage. The decolorized muscadine pomace solvent extract was better than the positive control (1 mM Trolox); treatment with compositions containing 0.25% TME after UVB exposure showed a reduction in DNA damage of between 38% and 44%, and treatment with compositions containing 0.1% TME reduced DNA damage by up to 69%.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of producing a decolorized muscadine grape pomace extract with lowered condensed tannin content, the method comprising:
    (a) preparing a precursor muscadine grape pomace extract from muscadine grapes,
    (b) clarifying the precursor muscadine grape pomace extract by microfiltration to remove solids, thereby producing a clarified extract,
    (c) processing the clarified extract by ultrafiltration through an about 500 to about 5000 kDa microfiltration membrane to obtain a first permeate and a first retentate, wherein flavor components are removed in the first permeate, and
    (d) processing the first retentate by ultrafiltration through an about 25 to an about 100 kDa ultrafiltration membrane to obtain a second permeate and a second retentate,
        wherein polymeric condensed tannins are retained in the second retentate and the second permeate has increased levels of polyphenols and lowered levels of sugars and condensed tannins compared to the first retentate, thereby producing the decolorized muscadine grape pomace extract with a tannin content that is lower than the clarified extract.

2. The method of claim 1, further comprising treating the second permeate with an odor-reducing agent.

3. The method of claim 2, wherein the odor-reducing agent is activated charcoal, calcium alginate, bentonite, or aluminosilicate absorbents.

4. The method of claim 1, further comprising exposing the second permeate to magnesium oxide to mineralize organic acids in the second permeate.

5. The method of claim 1, further comprising drying and milling the second permeate to produce a topical composition having a lowered tannin content as compared to the clarified extract, while substantially retaining a polyphenol content of the clarified extract.

6. The method of claim 1, wherein clarifying the extract comprises diluting the extract with water, and subjecting the diluted extract to the microfiltration.

7. The method of claim 6, wherein the microfiltration is performed through about a 200 kDa microfiltration filter.

8. The method of claim 1, wherein the muscadine grapes comprise bronze and/or purple muscadine grapes.

9. The method of claim 8, wherein the muscadine grapes comprise a combination of bronze and purple muscadine grapes.

10. The method of claim 9, wherein the ratio of bronze muscadine pomace extract to purple muscadine pomace extract ranges from a) 0.1 to 10 (weight to weight) or b) from 0.3 to 3 (weight to weight).

11. The method of claim 9, wherein the precursor grape pomace extract is obtained by a) separate extraction of bronze and purple muscadine grapes with subsequent combination of the resulting extracts; or b) by simultaneous extraction of bronze and purple muscadine grapes combined in desired ratios.

12. A decolorized muscadine grape pomace extract obtained by the method of claim 1.

13. The decolorized muscadine grape pomace extract of claim 12, wherein the extract comprises about 9% to about 10% polyphenols and less than about 4% monosaccharides, and wherein the condensed tannins are less than about 10% of the total polyphenol content of the decolorized muscadine pomace extract.

14. The decolorized muscadine grape pomace extract of claim 13, wherein the total polyphenols in the extract consist of at least about 90% polyphenols other than condensed tannins.

15. A skin care composition comprising an effective amount of the decolorized muscadine grape pomace extract of claim 13.

16. A method for treating skin, comprising contacting skin of a subject with an effective amount of the decolorized muscadine grape pomace extract of claim 13, thereby a) inhibiting elastase, collagenase or tyrosinase in the skin; b) reducing DNA damage; c) enhancing DNA repair, d) inhibiting glycation of cutaneous proteins, or e) increasing cell survival upon exposure to ultraviolet light; and/or f) increasing antioxidant activity, in the skin of the subject.

17. A topical composition comprising an effective amount of:
    (a) the decolorized muscadine grape pomace extract of claim 13,
    (b) beta-glucan, and
    (c) grape seed extract.

18. A method of reducing inflammation of skin in a subject, comprising:
    applying to the skin of a subject the topical composition of claim 17, thereby reducing inflammation in the skin of the subject.

19. The method of claim 18, wherein reducing inflammation comprises reducing the production of at least one of IL-1 alpha, IL-6, or prostaglandin E2, in a cell of the skin as compared to a control cell.

20. The method of claim 18, wherein the control cell is an untreated cell; wherein the control cell is a cell treated with a carrier; or wherein the inflammation is a result of exposure to ultraviolet radiation.

21. The method of claim 18, wherein reducing inflammation comprises reducing the production of an inflammatory mediator in a skin cell.

22. The method of claim 21, wherein the inflammation is a result of exposure of the subject to ultraviolet radiation and/or wherein the inflammatory mediator is IL-1 alpha, IL-6 or prostaglandin E2.

23. The method of claim 18, wherein the subject is a healthy subject.

24. The topical composition of 17, wherein the composition further comprises at least one of panthenol, Vitamin C or superoxide dismutase in a sufficient amount to reduce production of at least one of IL-1 alpha, IL-6, prostaglandin E2, or any combination thereof, in the skin when applied topically.

25. The topical composition of claim 17, wherein the composition further comprises an effective amount of Vitamin A, Vitamin E, or both.

26. The topical composition of claim 24, wherein the composition comprises by weight of the topical composition,
    about 0.0001% to about 0.5% Vitamin A,
    about 0.00001 to about 0.1% Vitamin C,
    about 0.001% to about 1.0% Vitamin E,
    about 0.001% to about 1.0% panthenol,
    about 0.00001% to about 0.1% superoxide dismutase,
    or any combination thereof.

27. The topical composition of claim 17, wherein the composition further comprises Vitamin C in the form of magnesium ascorbyl phosphate; Vitamin A in the form of Vitamin A palmitate; Vitamin E in the form of Vitamin E acetate; or any combination thereof.

28. The topical composition of claim 17, wherein the decolorized muscadine pomace extract comprises a combination of bronze and purple muscadine grape pomace extracts, and wherein the ratio of bronze muscadine pomace extract to purple muscadine pomace extract of the decolorized muscadine pomace solvent extract ranges from about 0.1 to about 10 (weight to weight), or from about 0.3 to about 3 (weight to weight).

29. The topical composition of claim 17, wherein
   a) the decolorized muscadine pomace extract comprises about 7% to about 10% polyphenols and less than about 5% monosaccharides by weight of the extract, and wherein the condensed tannins are less than about 10% of the total polyphenol content of the decolorized muscadine pomace extract;
   b) the decolorized muscadine pomace extract comprises about 9% to about 10% polyphenols and less than about 4% monosaccharides by weight of the extract;
   c) the total polyphenols of the decolorized muscadine pomace extract consist of at least about 85% polyphenols other than condensed tannins; or
   d) the total polyphenols of the decolorized muscadine pomace extract consist of at least about 90% polyphenols other than condensed tannins.

30. The topical composition of claim 17, wherein the decolorized muscadine pomace extract comprises an extract of whole purple muscadine grapes, an extract of purple muscadine pomace from other than whole grapes, or both.

* * * * *